United States Patent
Lipshitz

(10) Patent No.: US 6,913,620 B2
(45) Date of Patent: Jul. 5, 2005

(54) INTRAOCULAR LENS IMPLANT WITH MIRROR

(76) Inventor: Isaac Lipshitz, 89A Hanassi St., Herzlyia (IL)

(*) Notice: Subject to any disclaimer, the term of this patent is extended or adjusted under 35 U.S.C. 154(b) by 208 days.

(21) Appl. No.: 10/316,006

(22) Filed: Dec. 11, 2002

(65) Prior Publication Data
US 2003/0187502 A1 Oct. 2, 2003

Related U.S. Application Data

(63) Continuation-in-part of application No. 10/108,458, filed on Mar. 29, 2002.

(51) Int. Cl.$^7$ .................................................. A61F 2/16
(52) U.S. Cl. ...................................... 623/6.32; 623/6.26
(58) Field of Search ........................... 623/6.11, 6.12, 623/6.13–6.22, 6.23–6.36

(56) References Cited

U.S. PATENT DOCUMENTS

| | | | | |
|---|---|---|---|---|
| 4,759,761 A | * | 7/1988 | Portnoy | 623/6.11 |
| 5,139,325 A | * | 8/1992 | Oksman et al. | 351/161 |
| 5,166,711 A | * | 11/1992 | Portney | 351/161 |

* cited by examiner

Primary Examiner—Corrine McDermott
Assistant Examiner—Hieu Phan
(74) Attorney, Agent, or Firm—Mark M. Friedman

(57) ABSTRACT

An intraocular implant for implantation into the interior of an eye is disclosed. The intraocular implant includes a body member, (the body member has an anterior surface and a posterior surface, and has optical properties,) and, at least one mirror, wherein the at least one mirror is contained within the body member.

6 Claims, 22 Drawing Sheets

INTRAOCULAR LENS IMPLANT WITH MIRROR

This is a Continuation-in-Part Application of U.S. patent application Ser. No. 10/108,458, filed on Mar. 29, 2002, now pending.

FIELD AND BACKGROUND OF THE INVENTION

The present invention relates to an intraocular insert for implantation in the interior of the human eye and, more particularly, to an intraocular implant with at least one mirror.

Macular degeneration is a disorder in which the central retinal area (the macula) degenerates, e.g., because of age (age-related macular degeneration, or AMD), diabetic retinopathy, ocular vascular accidents or diseases, retinal dystrophies (such as, for example, cone dystrophy), central nervous system (CNS) diseases, etc. These disorders in the macular area cause difficulty in central vision such that the afflicted person finds it difficult to read, drive, or perform other daily activities that require fine, sharp, central vision, but the individual's peripheral vision remains unaffected.

The normal eye usually functions in a manner such that central vision is used for focused vision, such as with reading, for example. The extraocular muscles move the globe of the eye so as to adjust the eye so that the image of an object being looked at impacts always on the point of central vision that occupies only a small fraction (less than 10%) of the retina, that is, the macula. The bulk of the retina is used for peripheral vision, which serves primarily for orientation in space and the visual acuity is not as sharp as that of the central vision of the macula. Thus central vision provides a relatively small field of view with very high resolution for perception of details, while peripheral vision provides a wide field of view with relatively low resolution, providing sufficient information for navigation and detection of targets of interest.

AMD is a common cause of visual loss among people over the age of 60. The risk of developing AMD is nearly 30% in those over age 75.

Low vision aids such as special telescopic or microscopic eyeglasses that create a magnification of the object on the retina have been used in the treatment of this condition. However, when an outside telescope is used, the visual field is very narrowly restricted, and therefore the afflicted person has to move his or her head back and forth to follow the lines being read. An alternative has been an intraocular implant containing a telescope (as described in Applicant's U.S. Pat. No. 5,354,335, U.S. Pat. Nos. 5,391,202, 5,814,103, 5,876,442, 5,928,283, 6,007,579 and 6,066,171). Laser photocoagulation and photodynamic therapy, as well as vitamin supplements, are also used in the treatment of this condition. Limitations to the use of the intraocular implants with a telescope include that these implants can not be used in both eyes—one eye (the implanted eye) is needed for improved central vision and one (the other eye, without the implant) for peripheral vision. The IOL with the telescope (also known as an implantable miniaturized telescope, or IMT) obscures peripheral vision and interferes with the pupillary opening. The IOL with the telescope has a black posterior part that does not allow light to enter the eye, except through the telescope, as that would cause stray light and glare. The pupil has to be narrowed so that the pupil covers at least some of the black part of the IMT. With use of the IOL with the telescope there is a considerable reduction in the amount of light that enters the eye. It is reduced by up to 9-fold for a 3× magnification, (that is, only ⅑ of the light enters the eye), depending on the size of the opening of the telescope's cylinder. Further, there is a limit to the amount of magnification permitted by the geometry and the size of the telescope so that one can not achieve higher magnification without further restricting the visual field. Furthermore, use in only one eye causes anisoconia with a difference in image size between the eyes. In addition, retinal treatment such as laser or photodynamic therapy is difficult to perform through an IOL with a telescope.

In addition, it would be desirable to have an intraocular implant that could be adapted so as to be used for treatment of other diseases and problems of the eye. For example, such an intraocular implant could be used for treatment of diseases and processes that cause constriction of peripheral vision, including inherited retinal disorders causing retinitis pigmentosa, and glaucoma as examples. Further applications for such an intraocular implant include increased image magnification, increased illumination and the elimination of certain wavelengths of light, such as ultraviolet light, as well as allowing depth perception with vision from a single eye by creating monocular stereopsis. An implant providing increased illumination and increased magnification would be desirable also for use in the treatment of regular cataract patients, who do not have retinal problems.

U.S. Pat. No. 4,759,761 to Portnoy discloses a catadioptric intraocular lens containing interior mirrored surfaces forming a folded telescope. The lens of the Portnoy patent suffers from many limitations similar to those of the IMT discussed hereinabove. In particular, the lens disclosed in U.S. Pat. No. 4,759,761 does not preserve and permit peripheral vision because the mirrors cover the entire pupillary aperture it does not preserve the full peripheral visual field. It would be desirable to have a device that increases central visual field but as well allows normal peripheral vision. The device of the Portnoy patent produces a limited magnified central visual field only. It would be desirable to have a device that permits a full normally sized visual field with a magnified central image for seeing precise objects such as for reading while preserving peripheral vision, without magnification, or with very small amounts of magnification, as well. Further, the device of the Portnoy patent is not structured so as be useful for other disease processes such as diabetic maculopathy, retinitis pigmentosa or advanced glaucoma. As the mirrors cover the entire pupillary aperture, it tries to achieve a maximal increased central image visual field while covering and obscuring the natural peripheral visual field and thus it is almost impossible to examine the retina or treat it, beyond the blockage of peripheral vision. As for the IMT with telescope, the device of Portnoy, which was never built or used in clinical practice, can only be implanted in one eye. This leads to several limitations including: anisoconia (difference in image size between the eyes); a difference in the angular velocity of moving objects between the eyes; and the need for prolonged rehabilitation due to the two eves having different visual performance: one eye for a magnified central visual field and the other for the normal peripheral visual field. Further, if, in the future, one eye severely deteriorates the patient cannot function with his only eye as he can see only either central vision or peripheral vision, but not both, with the device of Portnoy. The device of Portnoy has only two mirrors, which are concentric; it would be of benefit to have a device with more than two mirrors, as well as an implant in which the mirror was not necessarily a ring, and with different openings that disturbed the peripheral vision less.

There is thus a widely recognized need for, and it would be highly advantageous to have, an intraocular implant for treatment of defects in central vision, including AMD and other disorders of the macula, as well as increasing the central visual field while preserving peripheral vision, and other disorders of vision, such as regular cataracts, while preserving the natural unchanged peripheral visual field, devoid of the above limitations.

SUMMARY OF THE INVENTION

According to the present invention there is provided an intraocular implant for implantation in the interior of a human eye for treatment of defects in central vision, while preserving peripheral vision, and also for treatment of defects in the peripheral visual field.

According to one aspect of the present invention there is provided an intraocular implant for implantation into the interior of an eye, the eye having a pupil, an iris, and a retina, the retina having a macula, the implant including: a body member, the body member having an anterior surface and a posterior surface, and having optical properties, and, at least one mirror, wherein the at least one mirror is contained within the body member.

According to another aspect of the present invention there is provided an intraocular implant including a body member, the body member having a plurality of surfaces, and having optical properties, and, at least one mirror, wherein the at least one mirror is contained within the body member.

According to further features in preferred embodiments of the invention described below, the implant is adapted for a position of fixation into the eye, the position of fixation being selected from the group consisting of anterior chamber fixation, posterior chamber fixation, capsular bag fixation, scleral fixation, intra-vitreous fixation, sulcus fixation, and iris supported fixation.

According to still further features in the described preferred embodiments the anterior surface is of convex configuration.

According to still further features in the described preferred embodiments the posterior surface is of convex configuration.

According to still further features in the described preferred embodiments the posterior surface is of planar configuration.

According to still further features in the described preferred embodiments the body member is non-foldable.

According to still further features in the described preferred embodiments the body member is foldable.

According to still further features in the described preferred embodiments the implant further includes at least one loop for fixation in the eye.

According to still further features in the described preferred embodiments the at least mirror is configured so as to reflect a viewed image onto a preferred position of the retina of the eye.

According to still further features in the described preferred embodiments the at least one mirror is constructed from a plurality of separate component parts.

According to still further features in the described preferred embodiments the at least one mirror is adapted for multi-focal focusing.

According to still further features in the described preferred embodiments the at least one mirror is adapted for correction of higher order optical aberrations.

According to still further features in the described preferred embodiments the at least one mirror consists of two mirrors.

According to still further features in the described preferred embodiments the two mirrors are a central mirror and a peripheral mirror.

According to still further features in the described preferred embodiments the central mirror has a shape with at least one characteristic selected from the group consisting of convex, concave, astigmatic, prismatic, rounded, pointed, aspheric, irregular, fixed shape, and adjustable shape.

According to still further features in the described preferred embodiments the peripheral mirror has a shape with at least one characteristic selected from the group consisting of a complete circumferential ring, a partial circumferential ring, convex, concave, aspheric, circular, elliptical, astigmatic, prismatic, fixed shape, and adjustable shape.

According to still further features in the described preferred embodiments the peripheral mirror is at least partially hidden beneath the iris of the eye.

According to still further features in the described preferred embodiments the central mirror has at least one aperture therethrough.

According to still further features in the described preferred embodiments the implant further includes at least one adjustment mechanism for adjusting at least one feature of the at least one mirror.

According to still further features in the described preferred embodiments the adjustment mechanism is selected from the group consisting of a micromechanical mechanism, thermal mechanism, laser operated mechanism, ultrasound mechanism, an electromagnetic mechanism, a photoelectric mechanism, and a piezoelectric mechanism.

According to still further features in the described preferred embodiments the at least one feature is selected from the group consisting of shape of the at least one mirror, curvature of the at least one mirror, and position of the at least one mirror.

According to still further features in the described preferred embodiments the implant is adapted for the treatment of presbyopia by the adjustment of the feature and position of the at least one mirror.

According to still further features in the described preferred embodiments the at least one adjustment mechanism is operable from outside the eye.

According to still further features in the described preferred embodiments the at least one adjustment mechanism is operable from outside the eye by an adjustment control element selected from the group consisting of a laser, ultrasound, light, a frequency emitter, an electromagnetic force element, a temperature control element, and a pressure control element.

According to still further features in the described preferred embodiments the implant further includes at least one prism.

According to still further features in the described preferred embodiments the at least one prism is adapted so as to divert at least a portion of a viewed image to a preferred part of the retina of the eye.

According to still further features in the described preferred embodiments the at least one prism is adapted so as to produce a continuity on the retina of the eye of a reflected visual image with a transmitted, unreflected image.

According to still further features in the described preferred embodiments the at least one prism is selected from the group consisting of a holographic lens and a fresnel.

According to still further features in the described preferred embodiments the at least one mirror is coated with a reflectance altering material for altering at least one light reflectance property of the at least one mirror.

According to still further features in the described preferred embodiments the reflectance altering material is adapted for altering transmission of light through the implant.

According to still further features in the described preferred embodiments the reflectance altering material is adapted for blocking at least one specified spectrum of wavelength of light transmission through the implant.

According to still further features in the described preferred embodiments the implant further includes at least one filter for adjusting the light transmission through the implant.

According to still further features in the described preferred embodiments the implant further includes at least one lens.

According to still further features in the described preferred embodiments the implant further includes a conformer, the conformer adapted for implantation into a structure of the eye, the conformer and the body member being adapted such that the body member is capable of being inserted and fixed into the conformer.

According to still further features in the described preferred embodiments the conformer further includes at least one optical component.

According to still further features in the described preferred embodiments the conformer has at least one optical property.

According to still further features in the described preferred embodiments the conformer is non-foldable.

According to still further features in the described preferred embodiments the conformer is foldable.

According to still further features in the described preferred embodiments the conformer further includes at least one loop for fixation in the eye.

According to still further features in the described preferred embodiments the implant is adapted so that the body member may be changed within the conformer.

According to still further features in the described preferred embodiments the body member is solid.

According to still further features in the described preferred embodiments the body member encloses an inner cavity.

According to still further features in the described preferred embodiments the cavity is filled with a material with desired optical properties.

According to still further features in the described preferred embodiments the material is selected from the group consisting of a gas, air, a liquid, water, an oil, a solid, and a material with a graded index of refraction.

According to still further features in the described preferred embodiments the at least one mirror is adapted for transmission of a laser beam for medical purposes.

According to still further features in the described preferred embodiments the implant is adapted for inverting an image.

According to still further features in the described preferred embodiments the implant is adapted for magnifying an image According to still further features in the described preferred embodiments the implant is adapted for minifying an image.

According to still further features in the described preferred embodiments the implant is adapted for moving an image to a particular location on the retina.

According to still further features in the described preferred embodiments the implant is adapted for changing a visual field.

According to still further features in the described preferred embodiments the implant is adapted for increasing peripheral vision.

According to still further features in the described preferred embodiments the implant is adapted for improving central vision.

According to still further features in the described preferred embodiments the implant is adapted for altering an intensity of light entering the eye.

According to still further features in the described preferred embodiments the implant is adapted for altering at least one spectrum of wavelength of light entering the eye.

According to still further features in the described preferred embodiments the implant is adapted for treatment of a disorder of central vision.

According to still further features in the described preferred embodiments the disorder of central vision is age-related macular degeneration.

According to still further features in the described preferred embodiments the implant is adapted for treatment of a disorder of peripheral vision.

According to still further features in the described preferred embodiments the disorder of central vision is a tapetoretinal degeneration.

According to still further features in the described preferred embodiments the implant is adapted for treatment of a (normal) age related cataract.

According to still further features in the described preferred embodiments the peripheral visual field is preserved.

According to still further features in the described preferred embodiments the implant is adapted so as to be capable of being implanted into the eye containing the natural crystalline lens.

According to still further features in the described preferred embodiments any one of the plurality of surfaces of the body member is at least partially of a configuration selected from the group consisting of convex, concave, planar, aspheric, spheric, irregular, asymmetric, astigmatic, prismatic, holographic, fresnel, and graded index.

According to still further features in the described preferred embodiments the body member is at least partially foldable.

According to still further features in the described preferred embodiments the implant includes two mirrors, the two mirrors being configured as a Cassegrain telescope wherein the peripheral visual field of the eye is preserved.

According to still further features in the described preferred embodiments the implant includes more than two mirrors.

According to still further features in the described preferred embodiments the more than two mirrors is of a number chosen from the group consisting of three mirrors, four mirrors, five, or six mirrors; that is the implant includes three, four, five, or six mirrors.

According to yet further features in the described preferred embodiments each of the at least one mirror has a shape with at least one characteristic selected from the group consisting of a complete circumferential ring, a partial circumferential ring, a rectangle, convex, concave, rounded, pointed, aspheric, circular, elliptical, irregular, fixed shape, and adjustable shape.

According to still further features in the described preferred embodiments the implant further includes at least one adjustment mechanism for adjusting at least one feature of the at least one mirror, wherein the at least one adjustment mechanism is operable from inside the eye.

According to still further features in the described preferred embodiments the implant further includes at least one prism, wherein the at least one prism is of a type selected from the group consisting of a single prism, holographic lens, an axicon, a graded index element, and a fresnel.

According to still further features in the described preferred embodiments the implant further includes at least one filter for controlling the light transmission through the implant, wherein the control affects light transmission of a visual field of the eye selected from the group consisting of: at least part of the central visual field, at least part of the peripheral visual field, and at least part of both the central and peripheral visual fields.

According to still further features in the described preferred embodiments the filter is placed in a location selected from the group consisting of: on the at least one mirror, before the at least one mirror, after the at least one mirror, and so as to affect light that does not reflect on the at least one mirror.

According to yet further features in the described preferred embodiments the implant contains a plurality of mirrors, wherein all of the mirrors are placed within only a portion of the implant.

According to still additional features in the described preferred embodiments the portion is one lateral half.

According to still further features in the described preferred embodiments the implant has a central axis, and the implant further includes an optical diverting element for diverting light entering the implant to the at least one mirror, wherein the at least one mirror is placed at a location off the central axis.

According to still further features in the described preferred embodiments the optical diverting element is chosen from the group consisting of a prism, a holographic lens, an axicon, a graded index element, and a fresnel.

According to still further features in the described preferred embodiments the implant includes at least two mirrors.

According to still further features in the described preferred embodiments the implant further includes a conformer, the conformer adapted for implantation into a structure of the eye, the conformer and the body member being adapted such that the body member is capable of being inserted and fixed into the conformer, and the location of insertion being selected from the group consisting of a capsular bag, a vitreous, an iris support, an anterior chamber and a posterior chamber.

According to still further features in the described preferred embodiments the implant is adapted so as to permit monocular stereopsis.

According to still further features in the described preferred embodiments the at least one mirror includes at least three mirrors, such that light reflected from a first mirror and a second mirror of the at least three mirrors reflects onto a third mirror, the first mirror and the second mirror being configured so as to be at different precise distances from the retina so as to transmit simultaneously two different images onto the retina.

According to still further features in the described preferred embodiments the at least one mirror includes at least three mirrors, such that light reflected from a first mirror and a second mirror of the at least three mirrors reflects onto a third mirror, the first mirror and the second mirror being configured so as to be of different shapes so as to transmit simultaneously two different images onto the retina.

According to still further features in the described preferred embodiments the implant is adapted so as to be capable of being implanted into the eye containing at least one additional implant the at least one additional implant being of any type.

According to still further features in the described preferred embodiments the implant is configured for fixation into a location in the eye selected from the group consisting of a capsular bag, a sulcus, a vitreous, an anterior chamber, and a posterior chamber.

According to still further features in the described preferred embodiments the implant further includes at least one lens, wherein the at least one lens is placed in a location selected from the group consisting of within the implant, external to the implant and external to the implant with an attachment to the implant.

According to still further features in the described preferred embodiments the implant further includes at least one lens, wherein the at least one lens is adapted so as to permit the implant to perform a function selected from the group consisting of increasing magnification, decreasing magnification, changing a visual field, changing image location, improving an optical aberration and inducing an optical aberration.

According to still further features in the described preferred embodiments the at least one lens is selected from the group consisting of a holographic lens, a fresnel, and a graded index element.

According to still further features in the described preferred embodiments the implant is adapted for treatment of a disorder of the central visual field while presenting the peripheral visual field.

According to still further features in the described preferred embodiments the implant is adapted for treatment of a disorder of the peripheral visual field.

According to still further features in the described preferred embodiments the implant is adapted for treatment of a disorder of restricted peripheral vision.

According to still further features in the described preferred embodiments the implant is adapted for a function selected from the group consisting of magnifying at least part of an image, minifying at least part of an image, and moving at least part of an image to another location.

The present invention successfully addresses the shortcomings of the presently known configurations by providing an intraocular implant containing at least one mirror, which can be used in the treatment of any ocular problem, including disorders of central and peripheral vision. Whereas the IOL with a telescope is intended not to allow peripheral light to enter the eye as it causes visual disturbances, thus narrowing the pupillary opening, in the present invention the pupil is not affected and the pupil functions normally. Peripheral vision is permitted, in contrast to either the IOL with a telescope or the catadioptric intraocular lens of Portnoy, which tries to magnify and increase the visual field of the central magnified image, while totally obscuring the peripheral image.

In the IOL with a telescope there is a considerable reduction of the amount of light that enters the eye. In the IOL with a telescope, the amount of light entering the eye is reduced by up to 9 fold (only 1/9 of the light enters the eye), depending on the size of the opening of the telescope's cylinder, while all the other light is blocked. In the present invention there is no decrease of the amount of light that enters the eye, as the pupil is not affected. On the contrary the amount of light that enters the eye can be increased by using special coatings on the mirrors that collect more light and give better contrast.

In contrast with the device of the Portnoy patent, which, produces only a limited magnified central visual field, the present invention permits a full normally sized peripheral visual field with a magnified central image for seeing precise objects such as for reading while permitting normal peripheral vision for general orientation in space. The extraocular muscles move the globe of the eye so as to position the eye so that the image of an object always impacts on the point of central vision, that is, the macula. The remainder of the retina is used for peripheral vision, which serves primarily for orientation in space. Thus central vision provides a relatively small field of view with very high resolution for perception of details, while peripheral vision provides a wide field of view with relatively low resolution, providing sufficient information for navigation and detection of targets of interest.

Another advantage, among many others, of the present invention is the easing of restrictions of patient selection criteria for implantation, as use of the device is no longer restricted to patients that have similar visual acuities in both eyes, and visual acuity lower than a certain standard in both eyes. The present invention can be implanted in a patient that has central visual problems in both eyes without taking into account the relative visual acuity of the other eye. Further it can be used for both dry-type as well as wet-type macular degeneration. In addition, in contrast to the IOL with a telescope or the catadioptric intraocular lens of Portnoy, it can be used for other purposes including for treatment of defects in peripheral vision, for image magnification, including, for example, during regular cataract surgery, and for eliminating specific wavelengths of light such as ultraviolet light, for example.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
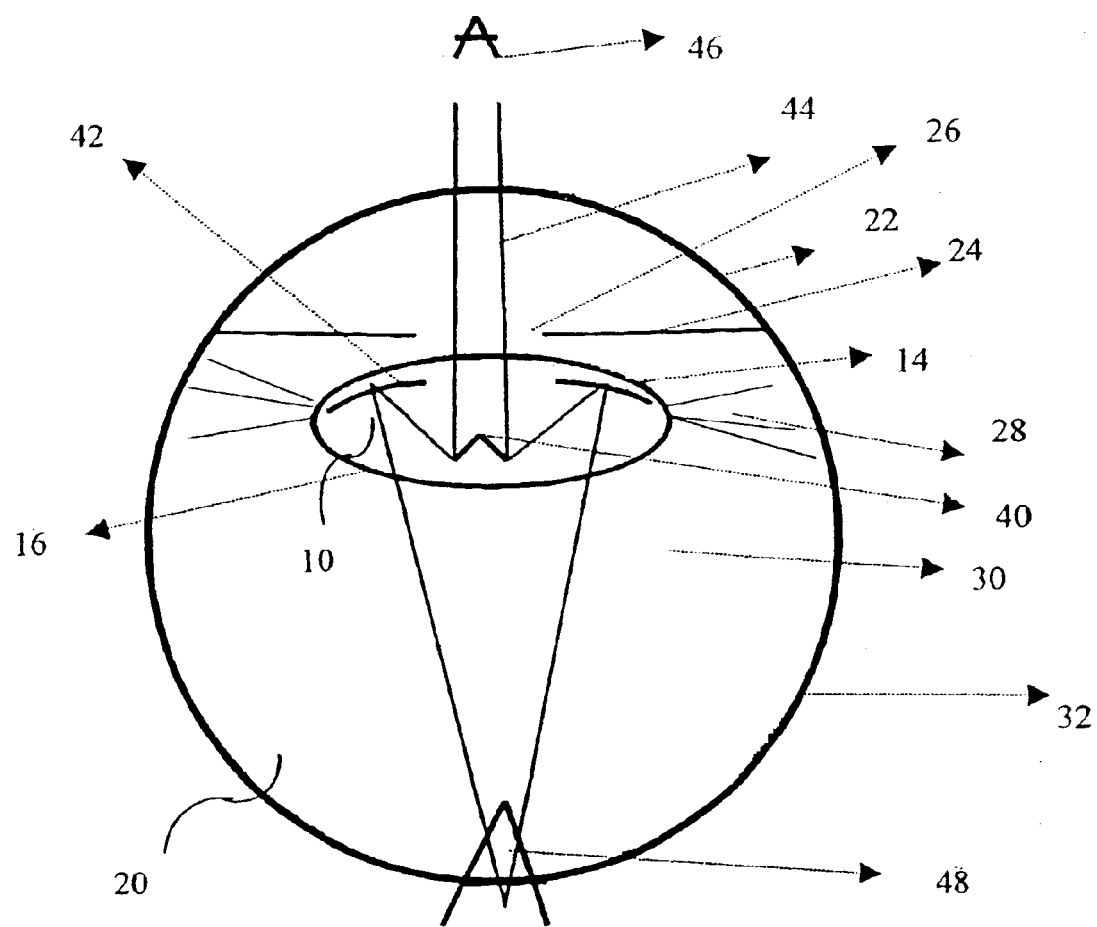
FIG. 1 illustrates a horizontal section of an eye with a preferred embodiment of the intraocular insert of the present invention in place.

The present invention is of an intraocular insert for implantation in the interior of the human eye and, more particularly, to an intraocular implant containing at least one mirror, which can be used in the treatment of regular cataracts, and of disorders of central, as well as of disorders of peripheral, vision. Specifically, the present invention can be used to treat AMD and other macular degenerations. Modifications of the intraocular insert can be used for the treatment of other ocular disorders including retinitis pigmentosa and glaucoma and other causes of impaired peripheral vision, for example.

The principles and operation of an intraocular implant containing at least one mirror according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and technology employed herein is for the purpose of description and should not be regarded as limiting.

Figure 22:
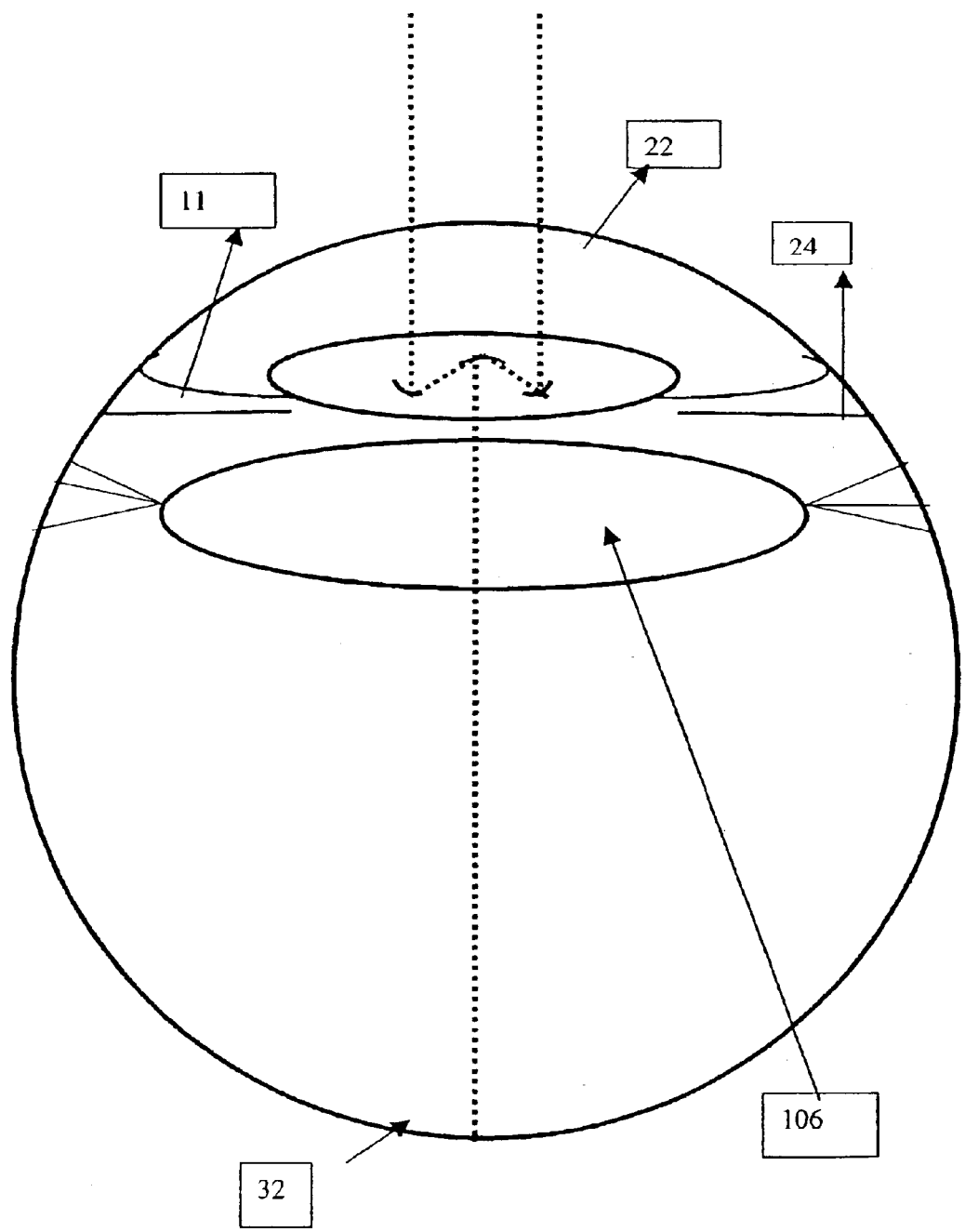

Referring now to the drawings, FIG. 1 illustrates a horizontal section of a human eye (20), illustrating the cornea 22, the iris 24, the pupil 26, the zonula 28, the vitreous 30 and the retina 32. FIG. 1 further illustrates a preferred embodiment of an intraocular implant, generally designated 10, constructed in accordance with the present invention, and implanted in eye 20. The means for fixing implant 10 in eye 20 are not described herein, as many such means are known for mounting artificial intraocular implants and lenses and can be used for fixing intraocular implant 10 in place. In various configurations of the present invention, implant 10 is implanted so as to replace the natural lens of eye 20, while in other configurations implant 10 is used in conjunction with the natural lens of eye 20 (see FIG. 22, which shows device 10 implanted in eye 20 where natural lens 106 remains in place). In various alternate configurations, implant 10 can be implanted in various compartments and by various techniques including fixation in the anterior or posterior chamber, capsular bag, by sulcus fixation, scleral fixation, intravitreous fixation or iris supported as non-limiting examples.

Figure 9:
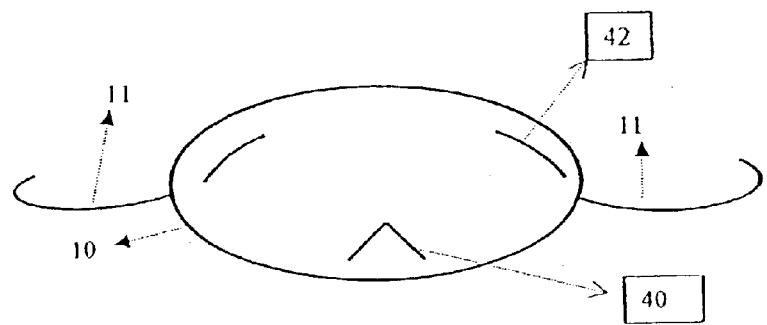
FIG. 9 is a horizontal section of a further alternate preferred embodiment of the intraocular insert according to the present invention.
Figure 9:
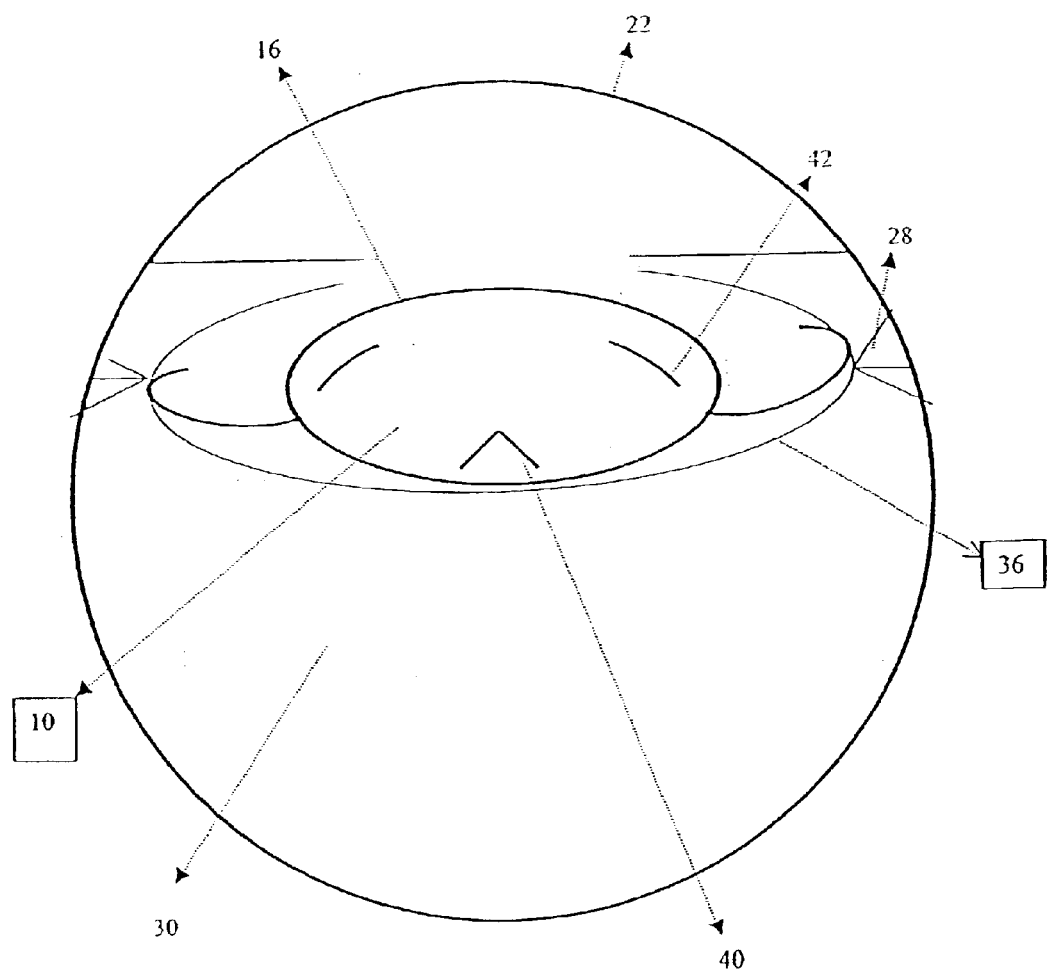

The intraocular implant 10 includes a body member 12, of generally convexo-convex or convexo-plano configuration; that is, its front or anterior face 14 facing the anterior side of eye 20 is of convex configuration, and similarly its rear or posterior face 16 facing the posterior side of eye 20 is of convex (or planar) configuration; or may be of any other geometrical configuration. For example, anterior face 14 or posterior face 16 may be at least partially of convex concave, planar spheric, aspheric, irregular, asymmetric, astigmatic, prismatic, holographic or graded index configuration, or some combination thereof. The dioptic and other optical properties of body member 12 are one parameter determining the visual correction of implant 10. Both surfaces may be of any dioptic power and may include additional optical properties such as a prism, fresnel, hologram, index graded optics or aspheric, as non-limiting examples. Body member 12 is generally fabricated from the same material as conventionally used for making intraocular lenses, such as a transparent plastic (e.g., polymethylmethacrylate, acrylic, or silicone), glass, sapphire or any other material suitable for use in the construction of intraocular implants. In various preferred embodiments, body member 12 may be made of a rigid material (and be a hard lens) or may be foldable (and be a soft lens), or may be made of a combination of both rigid and soft materials. Use of a material such as an acrylic or silicone that allows body member 12 to be soft and foldable allows the insertion of implant 10 through a smaller surgical incision. As illustrated in FIG. 9, implant 10 may also include at least one loop 11 for holding and fixing implant 10 inside the capsular bag 36 or in any other location inside of eye 20. Implant 10 fills the entire lenticular capsular bag 36 in certain configurations and applications, and in other configurations and applications does not fill the entire lenticular capsular bag 36. Particularly when implant 10 does not fill the entire capsular bag, various configurations of the at least one loop 11 fixes implant 10 within the capsular bag. In configurations where only one loop 11 is employed, loop 11 is preferably configured as a ring.

Figure 2:
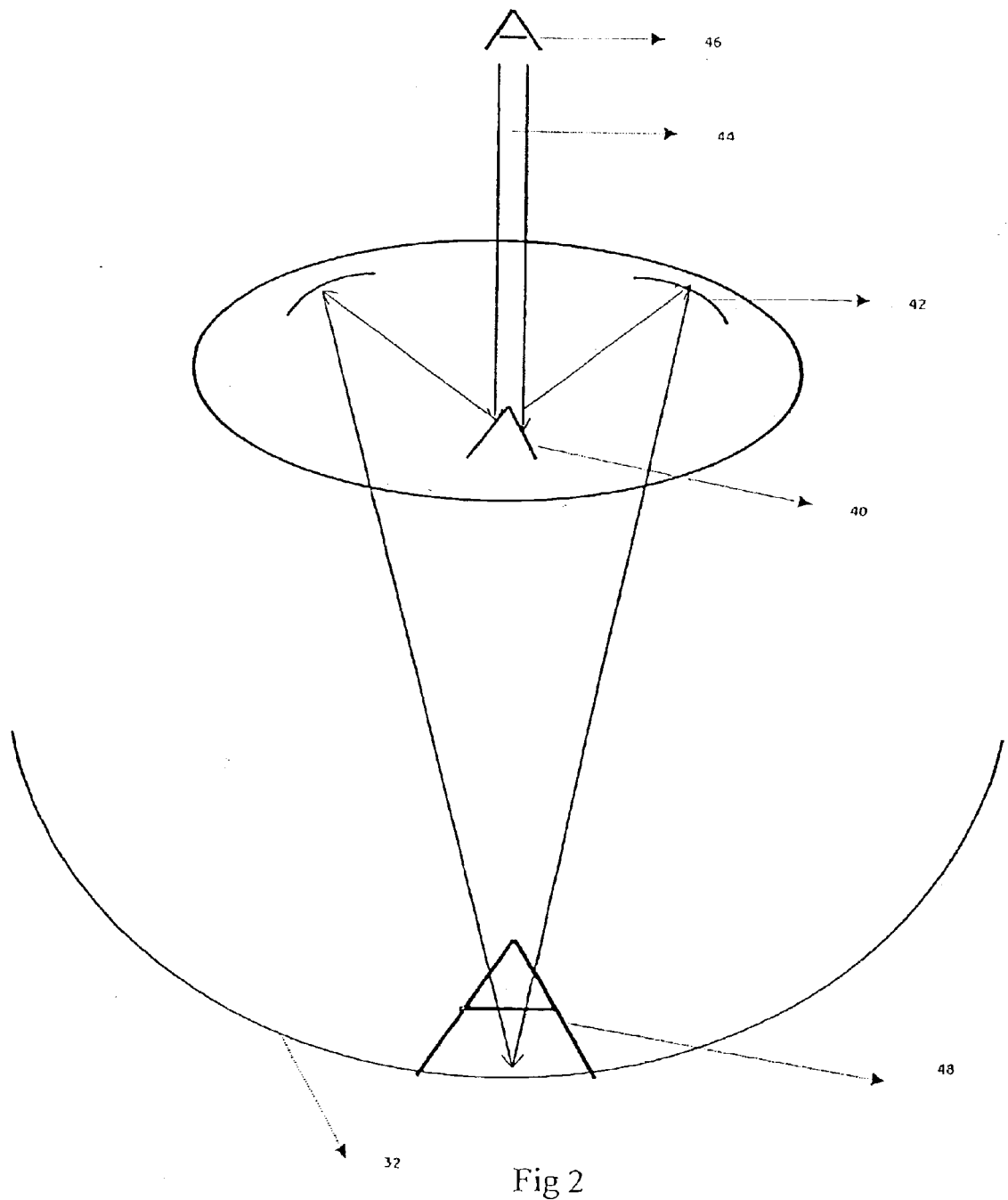
FIG. 2 is a schematic diagram illustrating the principles of a preferred embodiment of the present invention.

Incorporated into body member 12 of implant 10 is at least one mirror. Two are illustrated in FIG. 1 and are designated 40 and 42. This is for exemplary purposes only, and in other configurations only one mirror, or more than two, as illustrated below, are employed. The principle and object of implant 10 containing the at least one mirror is to improve vision, by changing the image on the retina. For example, implant 10 can be used to enlarge the central image on the retina of eye 20 in an individual affected with an ocular disorder such as AMD and can be used to reflect the image to a desired position on retina 32. As illustrated in FIG. 2, the at least one mirror, here illustrated in a non-limiting exemplary illustration with two mirrors, 40 and 42, function to gather light rays 44 of object 46 with a first, central mirror 40, and reflect the light to second (peripheral) mirror 42 before directing the light and focusing the image 48 on the retina 32. The arrangement of mirrors can be used to move, by use of mirrors or additionally prisms (as discussed hereinunder), the image to a preferred position on retina 32 where sight is, for example, better preserved than at the diseased portion of the macula. The arrangement of mirrors typically gives a wider aperture of vision and allows more flexibility of the geometric arrangement than a refracting telescopic system using lenses and avoids chromatic and other optical aberration, does not depend on the index of refraction of the media and enables preservation of the normal peripheral vision of the eye.

For the purposes of this specification and the accompanying claims, the term "mirror" is used to denote a reflective element, and to include any type of reflective element. Specifically included are such reflective elements including: a reflective mirror; a refractive lens with a posterior reflecting surface, wherein the anterior surface of the refractive lens may be either planar, spherical or aspherical, irregular, astigmatic, or prismatic, as non-limiting examples; and, a reflective holographic element or Fresnel surface, which may also be mounted on a posterior surface of a planar, curved, spherical or aspherical, irregular, astigmatic, prismatic element. In various configurations of the various preferred embodiments the at least one mirror may be concave, convex, aspheric, spheric, irregular, astigmatic, or prismatic or of any other geometric shape.

Thus there are essentially two parameters of implant 10 that determine the optical effect and visual correction produced by implant 10. The dioptric and other optical properties of body member 12 are one parameter determining the visual correction of implant 10, which affects both the central and peripheral vision. The second parameter is based on the properties of the optical performance of at least one mirror. As a non-limiting example, in particular preferred embodiment, the properties of body member 12 determine the correction of peripheral vision, but it affects also the central vision, and the magnification accomplished by the arrangement of the at least one mirror determines central vision. Normal light is transmitted directly and normally through body member 12 while central light is diverted to the at least one mirror. As such, "natural" or "regular" peripheral vision is permitted.

For the purposes of this specification and the accompanying claims, the phrase "natural" or "regular" peripheral vision is used to mean vision that is created by light that does not pass through or reflect upon the at least one mirror. This light may however be modified by other optical means (including increasing, decreasing, diverting or moving it as non-limiting examples) using optical systems located on the surface, inside implant 10 or connected to implant 10 from the outside. Thus use of the phrase "natural" or "regular" peripheral vision is specifically meant to also include vision that is optically changed not by the at least one mirror but through other optical means and projected on the peripheral (non-central) area of the retina. In certain configurations of the various preferred embodiments, as described hereinunder, implant 10 may further include lenses or other optical means to modify the central and/or the peripheral visual images.

Figure 3:
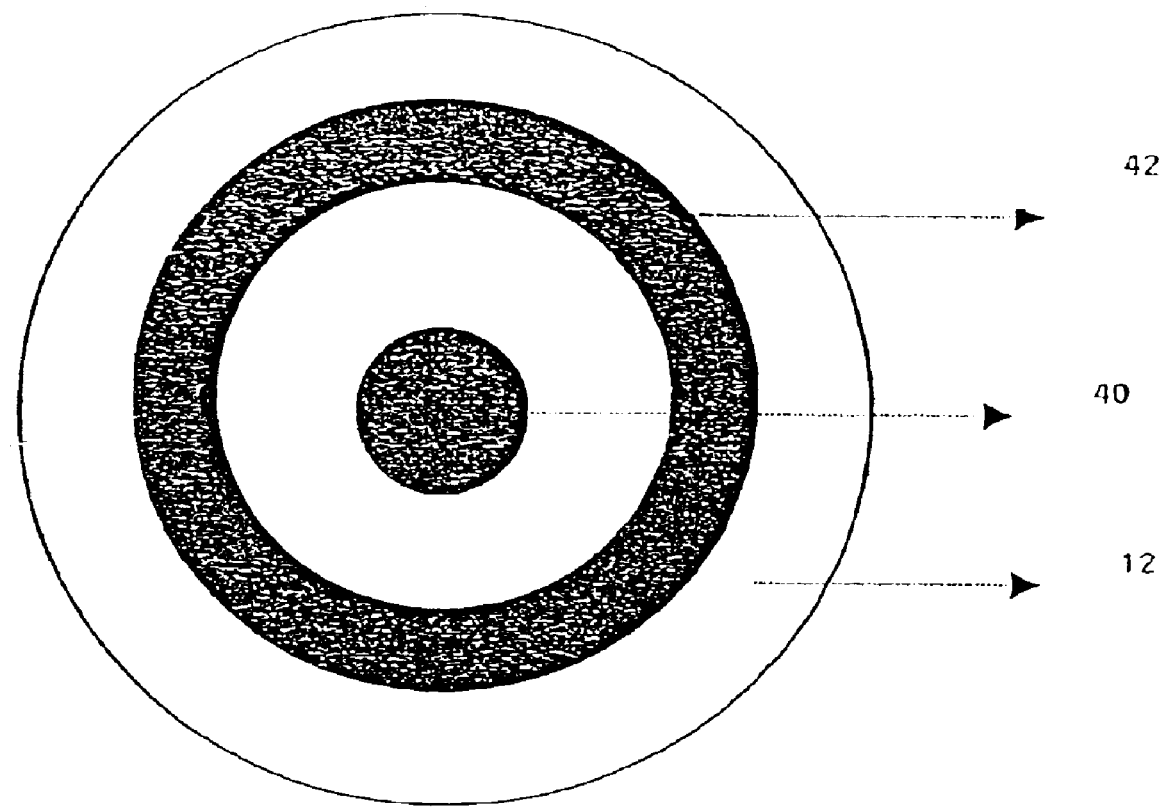
FIG. 3 is a frontal view of a preferred embodiment of the intraocular insert according to the present invention.

In various configurations, central mirror 40 may be convex or concave, and rounded or pointed and therefore take various shapes including, but not limited to shapes such as: U or ∩, V or Λ, as well as any other aspheric, irregular, astigmatic, or prismatic or irregularly shaped surface. Second mirror 42 is a circumferential ring (complete or partial, generally circular or elliptical, for example) hidden (completely or partially) beneath iris 24 as is illustrated in FIGS. 1 and 3. Alternatively an artificial pupillary aperture can be created by the mirror. Like reference numerals refer to like parts throughout the figures of the drawing. In such a position mirror 42 does not affect the passage of light rays into eye 20 as mirror 42 is under the iris 24 which already blocks the entry of light. Pupil 26 is not affected and functions normally (see FIG. 11, described further below). Thus the position of mirror 42 and, in some configurations, a gap in mirror 42, defines the size of pupil 26. Mirror 42 may take different shapes in various preferred embodiments, convex or concave or aspheric, as non-limiting examples, and may be of a fixed shape and (angle or degree of) curvature or may be adjustable as described hereinunder. In certain preferred embodiments (for example, where implant 10 is placed in the vitreous) only a single mirror is used. In others, more than two mirrors may be used, for example, to invert the image, or to increase the degree of magnification. In other configurations, for example, the at least one mirror can be used to make the image on the retina smaller, for example for the treatment of an anisometropia, or a wide angle mirror, like that used for rear or side view mirrors in an automobile can be employed to increase peripheral vision. Other purposes for different selections of different configurations of the at least one mirror include, for example, to improve the amount of light entering the eye or to eliminate certain wavelengths of light while permitting others. Further, the at least one mirror can be adapted for multi-focal focusing.

Central mirror 40, which is preferably about 0.1 to 4.5 mm, and more preferably 0.2 to 3.5 mm in size, and most preferably about 0.5 to 2 mm in size, can be placed in front of the macula of retina 32. Though mirror 40 may provide a small obstruction blocking light rays from directly impacting on the macula of retina 32, the macula is the portion of retina 32 that is damaged by the extant disease process in any case. In some embodiments central mirror 40 has an aperture (which may be centrally placed, as a non-limiting example) to allow direct and reflected light rays to pass therethrough and impact on retina 32. In such cases mirror 40 has a configuration that appears like / \ rather than Λ for example. Thus the at least one mirror may be constructed from more than one component part or piece. For example, the peripheral mirror 42 too may be constructed from separate pieces placed in various locations and not necessarily be continuous.

One of ordinary skills in the art would know how to operatively assemble the components of implant 10. Additional components may be required to connect and fix into place the various individual elements of implant 10.

In certain configurations, the at least one mirror is custom designed of a shape determined by the wave front of a specific eye and adapted so as to correct for higher order optical aberrations.

The size of the entire implant 10 is preferably about 4–10 mm in diameter, along the horizontal axis of the eye, (and most preferably 6–10 mm) by about 1–6 mm (and most preferably 4–5 mm), along the longitudinal axis of the eye, apart from any attached loops for fixation. The width of implant 10 along the longitudinal axis of the eye, is preferably less than the 5 mm size of the capsular bag, when implanted therein. When fixed in the vitreous, there is more space, and implant 10 may be of a larger size. Second mirror 42 is preferably about 0.2 to 5 mm in longest diameter.

Figure 10:
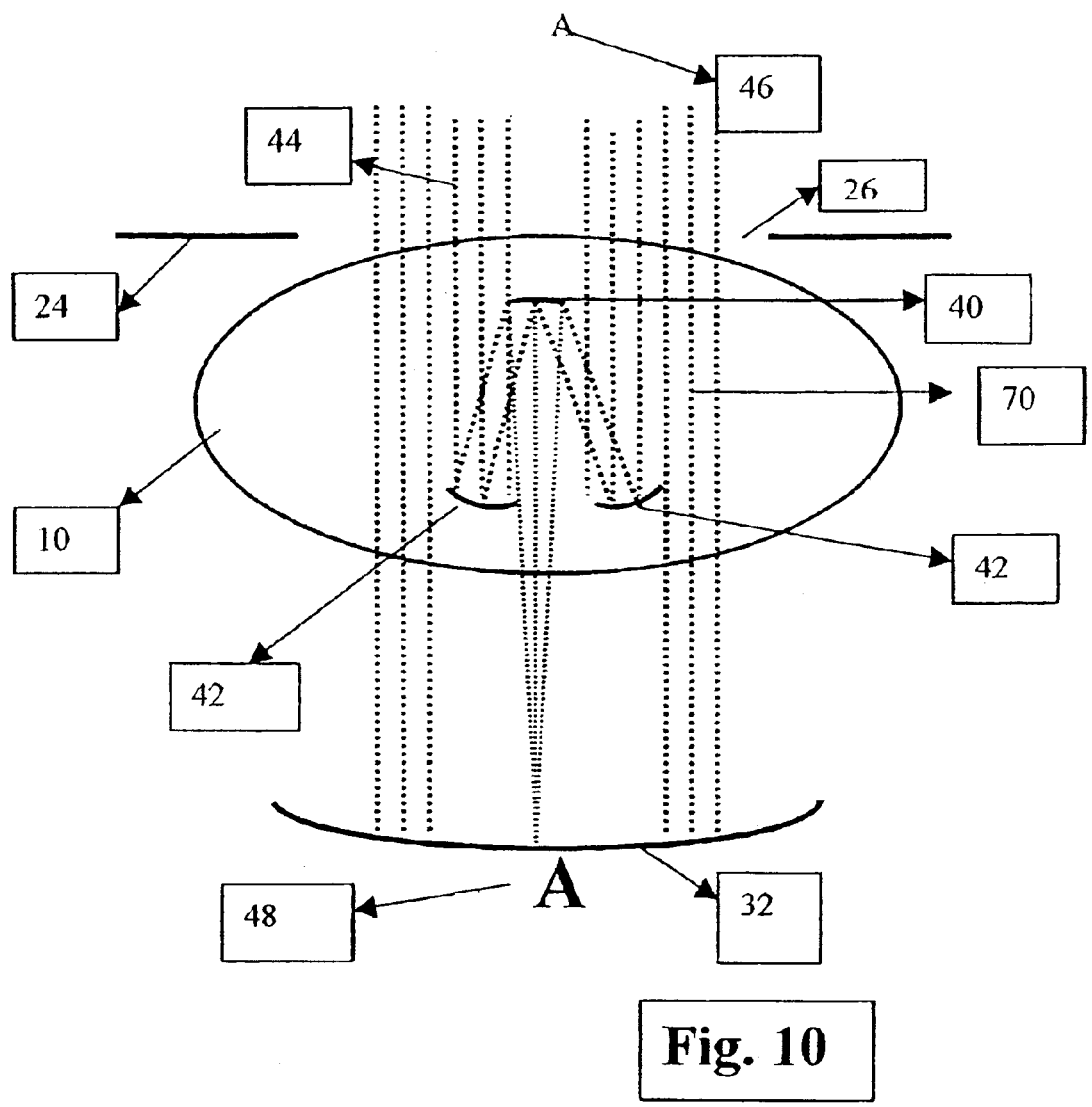
FIG. 10 is a horizontal section of another alternate preferred embodiment of the intraocular insert according to the present invention.

FIG. 10 illustrates a preferred embodiment of the present invention in which the arrangement of the at least one mirror takes the form of an intraocular Cassegrain telescope. Parallel light rays 44 of object 46 that are blocked from impacting directly on retina 32 because they are blocked by the coated back of central mirror 40 reflect off second mirror 42 which is preferably a circumferential ring as described hereinabove. The light rays reflected off mirror 42 is diverted to mirror 40 and from there reflected onto retina 32 where the photoreceptor cells transmit a now magnified image to the brain via the optic nerve. While the mirror arrangement improves central vision, normal peripheral vision is permitted in contrast to the device of U.S. Pat. No. 4,759,761, which only magnifies the central image and does not permit peripheral vision. The light 70 that passes through the device but does not impact on mirrors 42 and 40 is that of the normal peripheral vision, thus implant 10 allows the eye to see a central magnified image as well as a normal sized peripheral image.

Figure 11A:
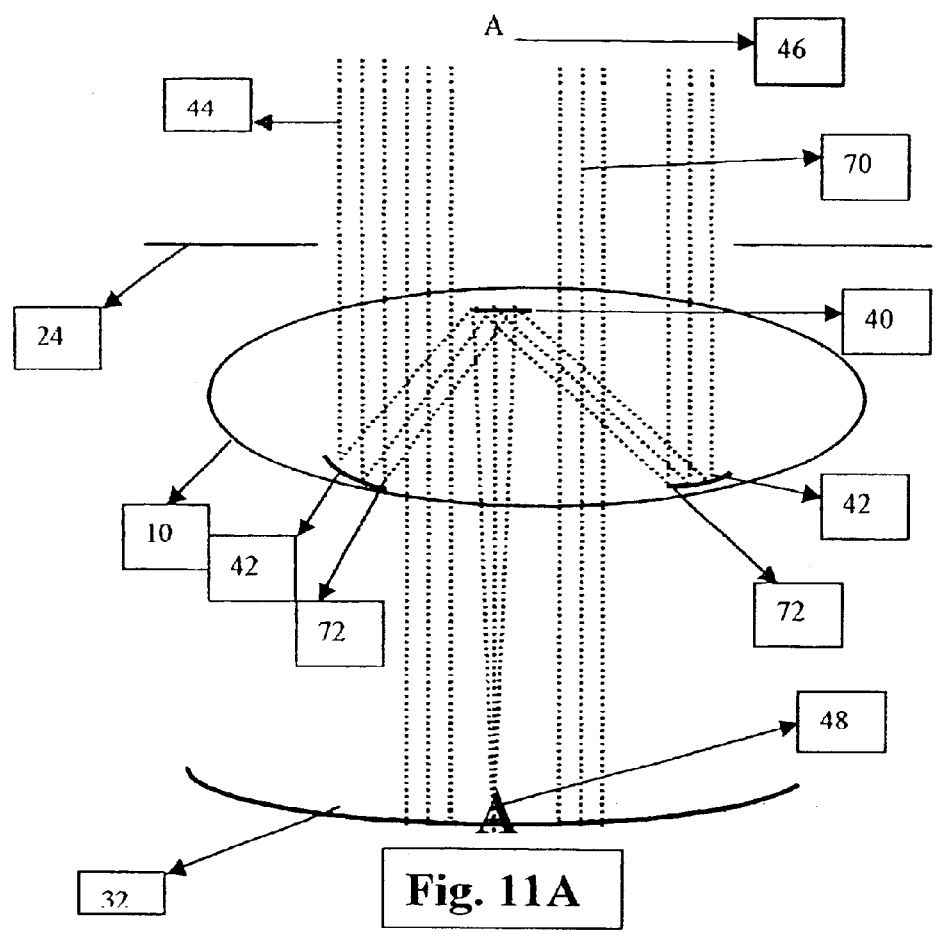
FIG. 11A is a horizontal section of another alternate preferred embodiment of the intraocular insert according to the present invention.
Figure 11B:
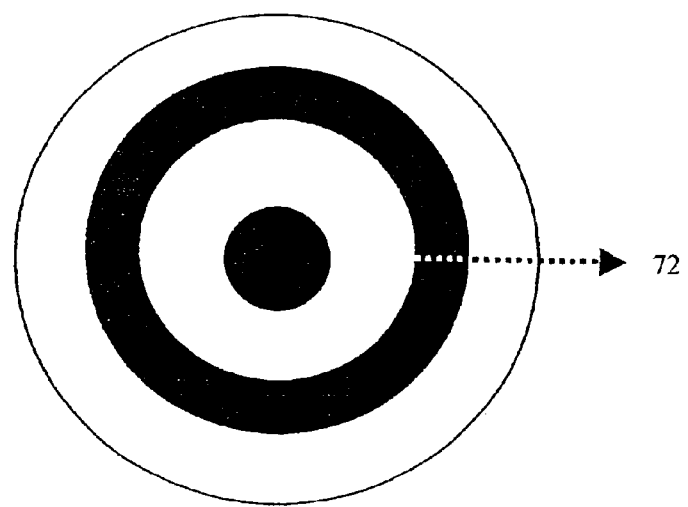
FIG. 11B is a frontal view of the alternate preferred embodiment of the intraocular insert according to the present invention illustrated in FIG. 11A.

FIG. 11 illustrates a further preferred embodiment similar to that illustrated in FIG. 10. The placement of mirror 42 differs in these 2 embodiments. In that illustrated in FIGS. 11A and B, mirror 42 is located more peripherally inside implant 10 such that the inner edges 72 of mirror 42 effectively create a pupillary opening. The peripheral placement of inner edges 72 of mirror 42 obstructs a smaller portion of the retina by mirror 42 permitting greater peripheral vision. The patient sees normal peripheral vision through a fixed pupillary opening defined by the inner edges 72 of mirror 42.

Figure 4:
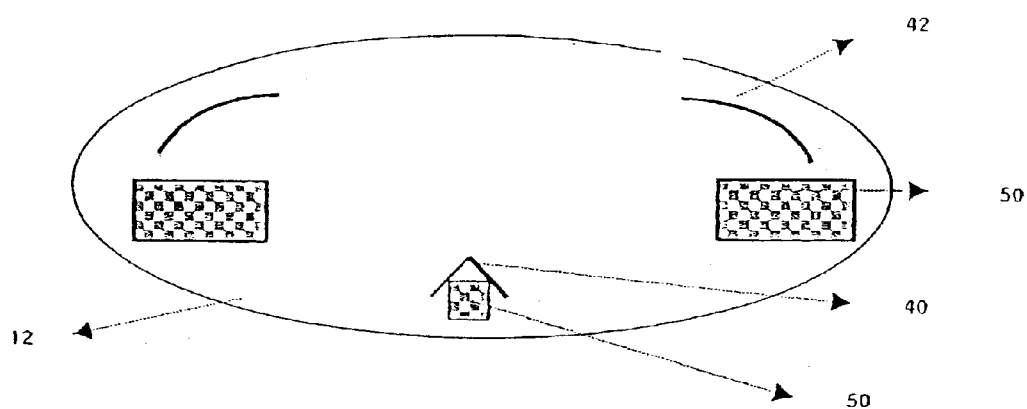
FIG. 4 is a horizontal section of an alternate preferred embodiment of the intraocular insert according to the present invention.

FIG. 4 illustrates a further preferred embodiment of the present invention in which the shape or curvature of the at least one mirror, for example, mirror 40 or mirror 42, is adjustable. Operationally connected to the at least one mirror (in various alternate configurations, either mirror 40 and/or mirror 42) is at least one adjustment mechanism 50. Adjustment mechanism 50 is operational from outside of or inside eye 20 to change the curvature of mirror 40 and/or 42 so as to change the magnification of image 48. Further adjustment mechanism 50 in certain configurations is adapted to move the position of the at least one mirror, for example in an anterior/posterior direction, to the sides, rotated, or tilted. Such movement in position of the at least one mirror 40 or 42 is particularly useful in the treatment of presbyopia. Adjustment mechanism 50 in certain embodiments contains, as a non-limiting example, a micromechanical element that exerts tractional forces on mirror 40 and/or 42 so as to change the curvature of mirror 40 and/or 42. Adjustment mechanism in other embodiments may also be an electromagnetic, a photoelectric, ultrasound, thermal effect, lasers, or piezoelectric element as further non-limiting examples. Adjustment mechanism 50 may include a power source (not illustrated individually) in certain configurations, which may be, as a non-limiting example, a photoelectric cell, or alternatively, utilize other sources for energy such as electromagnetic, temperature, ultrasound, laser or other sources. Such a power source in certain configurations is further used to move the position of implant 10 anteriorly and posteriorly, for example, or to change the pupillary opening and the refractive properties of the eye. Adjustment mechanism 50 is operable from outside eye 20, or from inside of eye 20, for example by a laser, light, ultrasound or other frequency emission, or an electromagnetic force, or for example, by a change in temperature, either heat or cold, or pressure. The degree of magnification of the implant is affected by the number shape, curvature and configurations of mirrors, the composition, shape and curvature of the body member, and any other optical elements placed in front of the eye such as lenses or spectacles.

Figure 5:
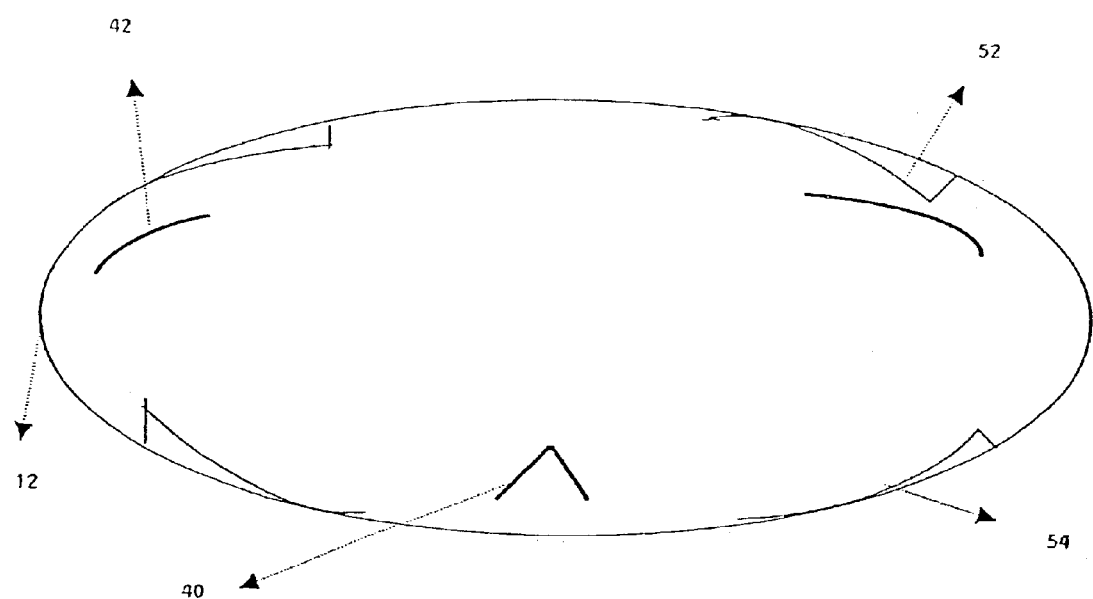
FIG. 5 is a horizontal section of a further alternate preferred embodiment of the intraocular insert according to the present invention.
Figure 21:
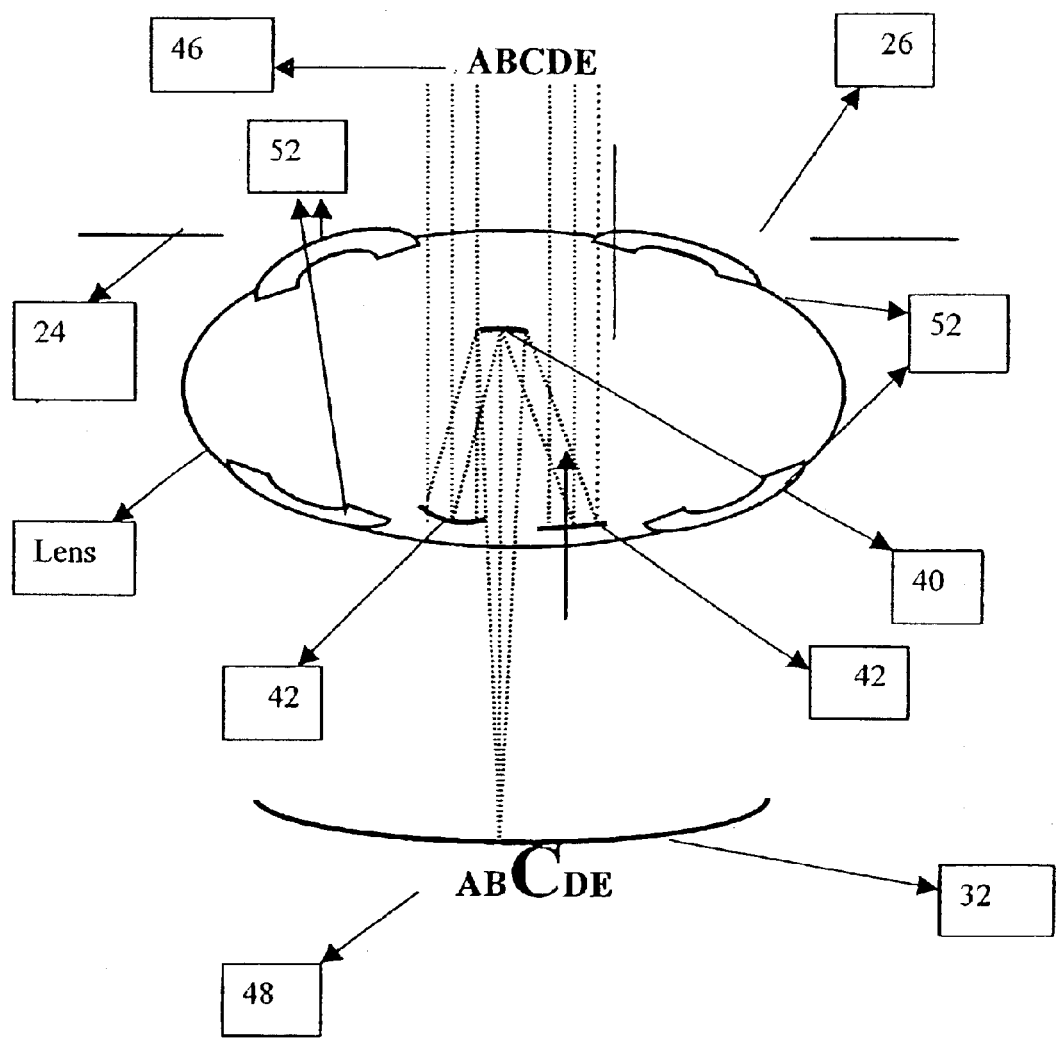
FIG. 21 is a horizontal section of yet another alternate preferred embodiment of the intraocular insert according to the present invention; and, FIG. 22 is a horizontal section of a still further alternate preferred embodiment of the intraocular insert according to the present invention.

FIG. 5 illustrates another preferred embodiment in which the intraocular implant 10 further includes at least one optical diverting element that moves the location of the image to another location, such as a prism 52. For the purposes of the specification and the accompanying claims, the word prism is used to include any optical element that gives a prismatic effect or displaces or moves the image to a new location. Prism 52 is used for example to divert all or portions of the vision, for example both central image 48 as well as the peripheral vision to other parts of the macula or of retina 32. At least one prism 52 can be placed in varying positions within implant 10 as illustrated in FIG. 5 by the illustrated second prism 54. The at least one prism (e.g. 52) can be used to avoid an improper overlap of the reflected image 48 with other images on retina 32. The at least one prism (e.g. 52) can be used to displace a peripheral image and make it in continuity with the magnified central image 48. The image from the central vision is now magnified while the peripheral visual field is normal and placed in continuity with the central image (as seen in FIG. 21). In order to smooth the picture seen and prevent overlap of a large central image on the smaller adjacent image, the at least one prism 52 pushes aside the peripheral image to make room for the large central image and to allow for a single continues smooth full picture. In various alternate preferred embodiments and configurations, the at least one prism 52 may be a separate element inside implant 10 (in those configurations wherein implant 10 is hollow) or the at least one prism 52 may be a holographic lens, a fresnel, axicon (a conical lens or rotationally symmetric prism), or be produced by a difference of index of refraction of the various materials of implant 10, or any other optical method for displacing an image, that is, changes the location of the transmitted image on the retina. Thus the at least one prism 52 may be inside or outside body member 12.

Further in certain configurations, the at least one mirror is coated with a material that alters the light reflectance properties of the at least one mirror. Such coating can be used for example, to collect more light and intensify the light transmission and the contrast of the reflected image as is desirable in patients with AMD. Further, alternate coatings can be used to block a certain spectrum of light (e.g. ultraviolet) so as to sharpen the image and also to reduce damage to retina 32. Further, in place of, or in addition to, the at least one prism 52, as illustrated in FIG. 5, implant 10 in certain preferred embodiments, contains at least one filter to change the spectrum of light impacting on retina 32. The filter can change the spectrum in the central visual field, the peripheral field or both. Such a change in spectrum can include both enhancements or reductions in the intensity or portion of the spectrum impacting on retina 32. The at least one filter may be placed on a mirror, between mirrors, before or after a mirror, or in such a manner as to affect light that does not impact on a mirror, within implant 10 or outside of implant 10, in order to change a parameter of the central visual field, the peripheral visual field, or both. The at least one filter may be used as a further non-limiting example, match the intensities if light of the two visual fields. In other preferred embodiments, at least one other optical component, for example at least one lens, may also be included in implant 10.

In alternate configurations, the precise arrangements of the at least one mirror (including the numbers, shapes, curvature, placement, and coating, for example, of the mirrors, as well as the presence of prisms or filters) can be used to determine the precise changes of the images reflected onto retina 32. Depending on the values for these parameters, implant 10 can be used to, as non-limiting examples, magnify, minify, move, or invert an image, increase or decrease the visual field, or introduce a prismatic inversion or change the intensity and/or spectrum of light entering the eye.

Defects in peripheral vision occur in other disorders of the eye, such as (inherited) tapetoretinal degenerations causing retinitis pigmentosa, and glaucoma for example. Peripheral vision involves the ability to perceive objects, gross movement, or sharp contrasts toward the sides and edges of the visual field. Use of a configuration of implant 10 in which the at least one mirror increases the visual field, for example through use of a wide angle mirror such as is conventionally employed in rear view car mirrors, can be used to treat such disorders and increase their visual field which otherwise suffer from reduced peripheral vision.

Figure 12:
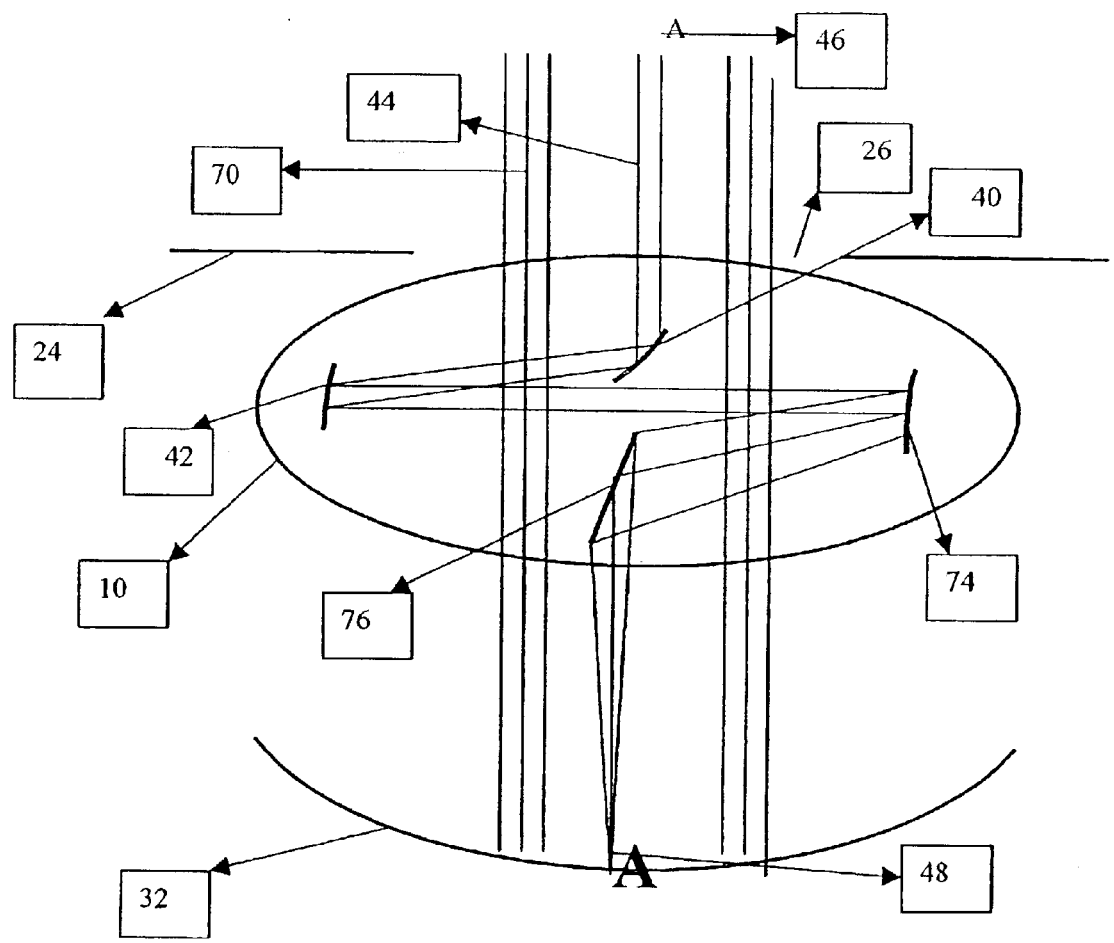
FIG. 12 is a horizontal section of another alternate preferred embodiment of the intraocular insert according to the present invention.
Figure 13:
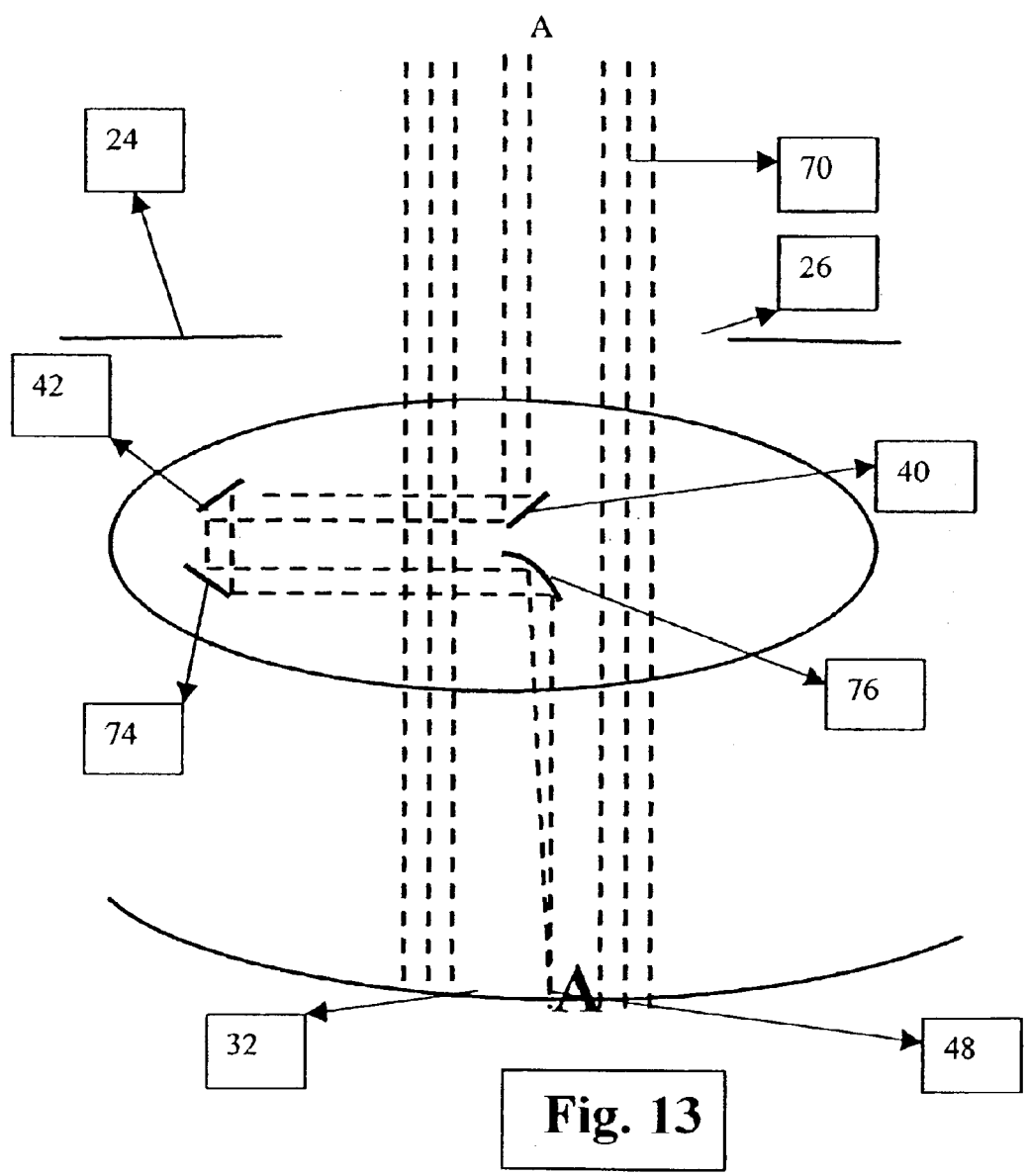
FIG. 13 is a horizontal section of another alternate preferred embodiment of the intraocular insert according to the present invention.
Figure 14:
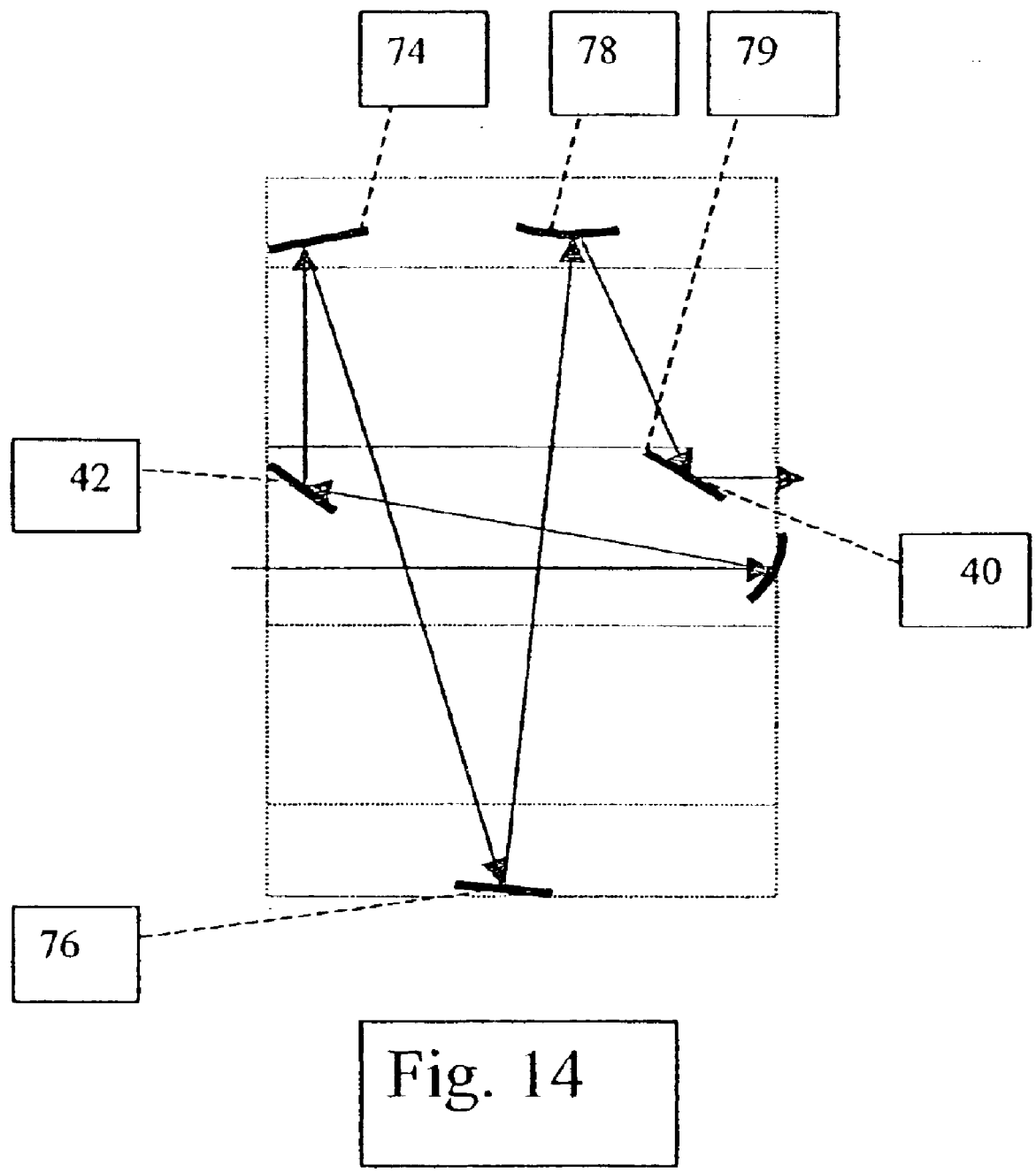
FIG. 14 is a horizontal section of another alternate preferred embodiment of the intraocular insert according to the present invention.

FIGS. 12–15 illustrate further alternate preferred embodiments of the present invention in which there are alternative arrangements of the at least one mirror. The principles of the embodiments illustrated in FIGS. 12–15 are the same as those illustrated in FIGS. 1 and 10, however in the embodiments of FIGS. 12–14, additional mirrors are employed. In FIGS. 12 and 13 for example, 4 mirrors are employed [labeled 40, 42, 74, and 76], and in FIG. 14 five mirrors are shown [labeled 40, 42, 74, 76, and 78]. In other embodiments other numbers of mirrors, more or less, can be used. The light can be diverted from side to side with implant 10 as seen in FIG. 12 for example, or may be in any other suitable configuration. As a non-limiting example, FIG. 13 illustrates a configuration in which all the mirrors are located in only a portion (here one lateral half) of implant 10. In all these embodiments, peripheral vision is preserved as the natural peripheral vision is not diverted by the at least one mirror, goes to the peripheral retina, and gives a normal sized, non-magnified image. The peripheral image may be changed optically through the use of additional optical elements but not through the mirror. The specific arrangement of the mirrors, including the size, mirror shape and configuration, mirror surface shape and configuration, placement, curvature, numbers and arrangement of the at least one mirror, is chosen so as to change the visual image in the desired manner, such as magnifying or minifying, or changing the location of the image, or changing the spectrum of light of the image, as non-limiting examples. Optical image 48 will be changed according to curvature, shape, structure, placement and other properties of the mirrors and the path which the reflected light follows. Any of the at least one mirrors may have any of various shapes including those described hereinabove such as a complete circumferential ring, and a partial circumferential ring, a rectangle, or any other regular or irregular geometric shape, and the surfaces of each mirror can be of various configurations including convex, concave, rounded, pointed, aspheric, circular, elliptical, irregular, fixed shape, and adjustable shapes, as non-limiting examples or a combination of the above.

Figure 15:
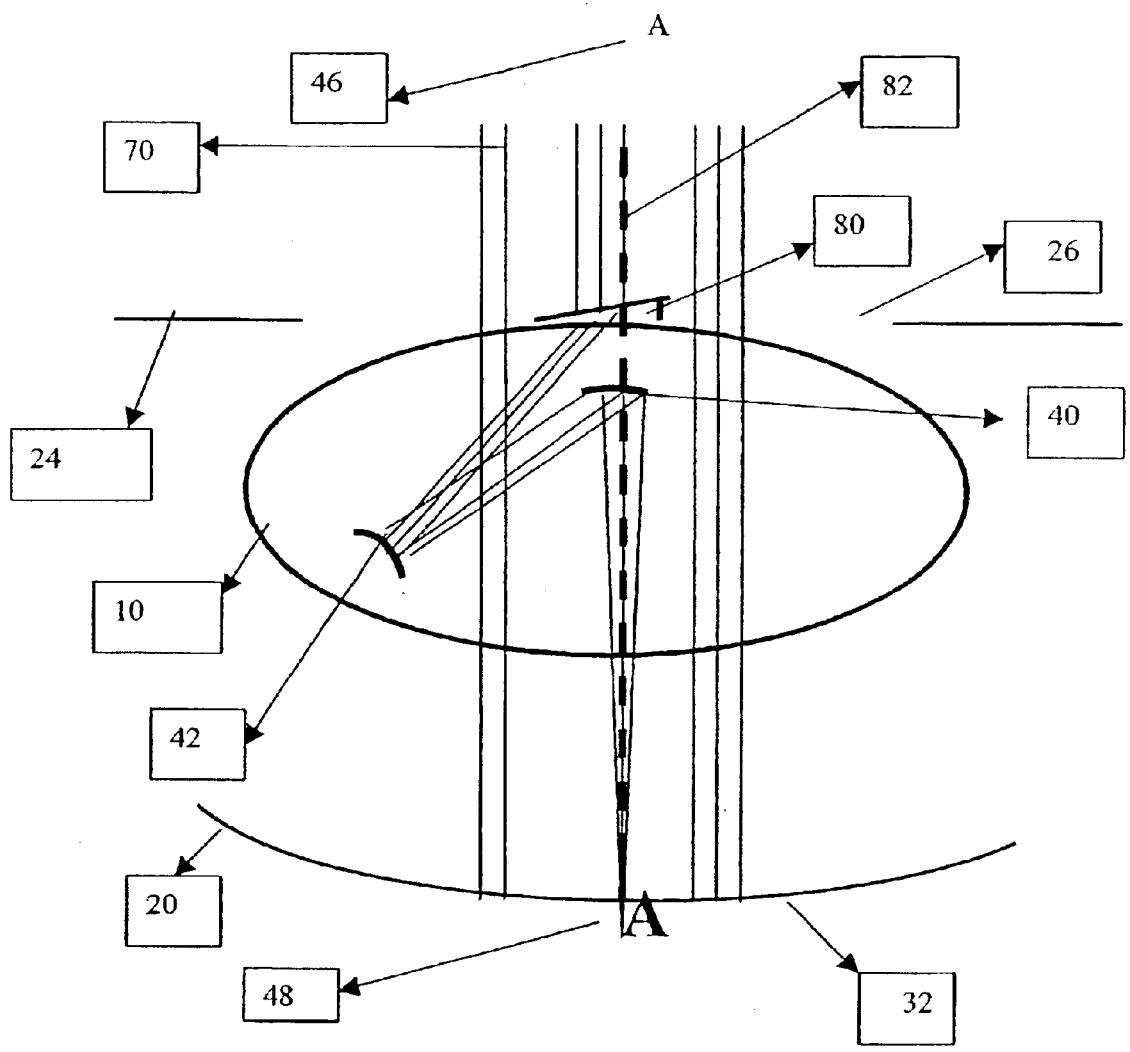
FIG. 15 is a horizontal section of another alternate preferred embodiment of the intraocular insert according to the present invention.

FIG. 15 illustrates yet another preferred embodiment of the intraocular implant according to the present invention. This embodiment employs an optical element 80 to divert light beam 44 from the central axis 82 of eye 20 to mirror 42 located at a position off central axis 82. Optical element 80 may be, for example, a prism or any other optical element such as a hologram, graded index material, a fresnel, axicon, or other similar optical element that can be used to divert an optical beam. Off axis mirror 42 can comprise a small or a larger portion of the pupillary opening 26, but in general is not always a fully circumferential mirror as described hereinabove. Light diverted to off axis mirror 42 is from there reflected to at least one additional mirror 40 and from there onto retina 32. Optical image 48 will be changed according to curvature, shape, structure, placement and other properties of the mirrors and the path which the reflected light follows. This design further preserves mostly undisturbed normal peripheral vision through light that passes through pupil 26 but that is not diverted through optical element 80 and mirror 42.

Figure 6:
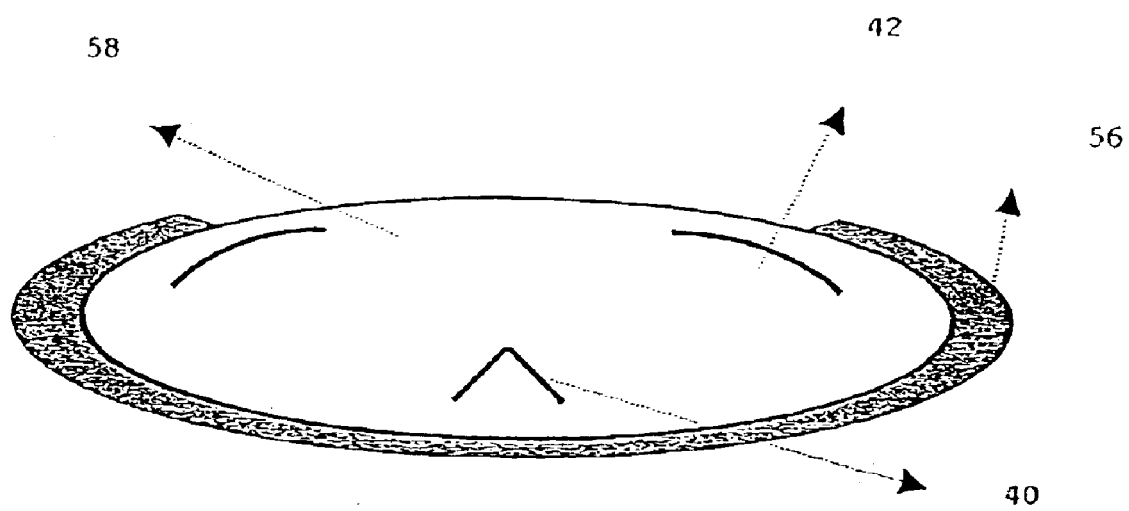
FIG. 6 is a horizontal section of a further alternate preferred embodiment of the intraocular insert according to the present invention.

FIG. 6 illustrates an alternate preferred embodiment of the implant 10 according to the present invention in which a carrier or conformer 56 is first inserted into a structure of the eye 20 (for example, to replace the patient's lens) and then body member 12 is inserted into conformer 56 as an inner insert 58. In this manner, inner insert 58 including body member 12 containing the at least one mirror can be more easily changed so as to change the treatment as the underlying disease changes and progresses. Further inner insert 58 can be rotatable from outside eye 20 or the position of inner insert 58 inside the eye can be changed in any other manner from outside the eye, by adding a mechanical or other mechanism, to rotate insert 58 within conformer 56. Conformer 56 may, in certain configurations, also contain various optical components such as at least one lens or mirror or conformer 56 itself may have various optical properties. As is described hereinabove for body member 12 conformer 56 may be constructed from a hard (non-foldable) or soft (foldable) material. Conformer 56 placed in any structure of the eye, generally preferably into the lenticular capsule as a non-limiting example, and, in certain configurations, has at least one loop (not illustrated), analogous to the at least one loop 11 illustrated in FIG. 9 for fixation to an eye structure. Conformer 56 may be implanted not only in the capsular bag, but also, in other configurations, in other sites such as the vitreous, iris support, anterior chamber or posterior chamber as non-limiting examples.

Figure 7:
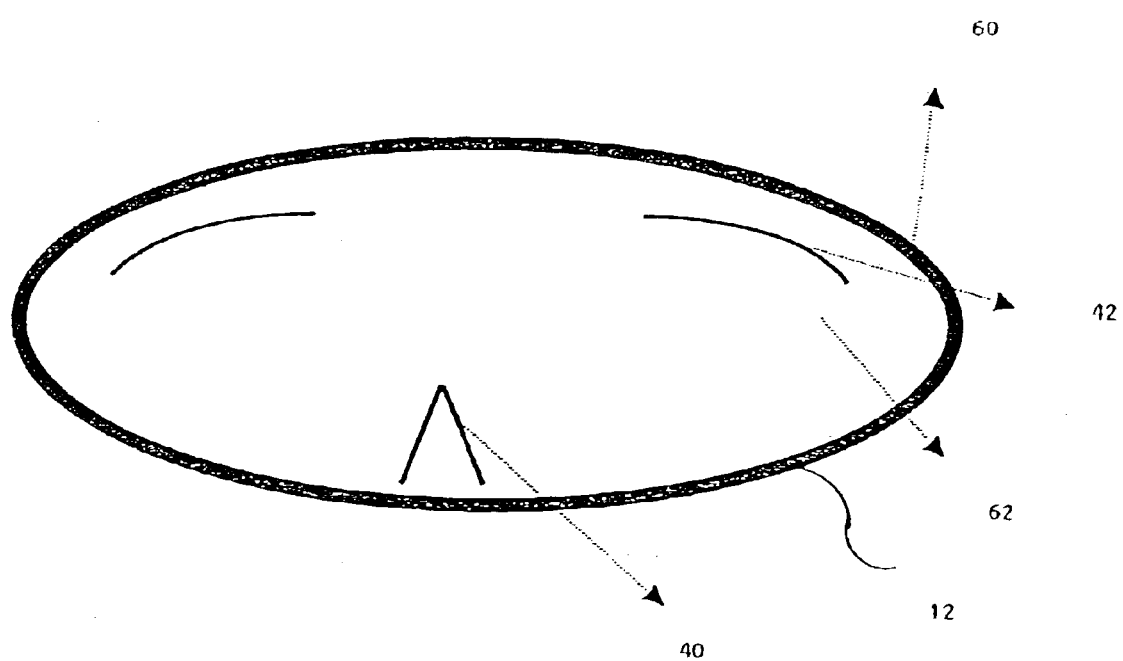
FIG. 7 is a horizontal section of a further alternate preferred embodiment of the intraocular insert according to the present invention.

FIG. 7 illustrates an alternate embodiment of implant 10 in which body member 12 is hollow rather than solid. Also envisioned are embodiments in which body member 12 is divided into several compartments. In the embodiment illustrated in FIG. 7, body member 12 consists of an outer casing 60, fabricated from glass or any other biocompatible and suitable material, enclosing an inner cavity 62. In such configurations wherein body member 12 is not fabricated from a biocompatible material, body member 12 is isolated from other ocular structures by a solid cover which is non-permeable to the toxic molecules. In embodiments such as that illustrated in FIG. 7, in which body member 12 is hollow, anterior and posterior surfaces 14 and 16 each have both outer and inner surfaces, the inner surfaces being those closest toward cavity 62. Each of these surfaces, that is the inner and outer surfaces of the anterior and posterior faces, may be of any geometrical configuration. For example, each may be at least partially of convex, concave, planar, spheric, aspheric, irregular, asymmetric, prismatic, holographic or graded index configuration, or some combination thereof. The at least one mirror (two are illustrated in FIG. 7 and are designated 40 and 42) are placed and fixed (as necessary with fixation elements) within cavity 62. Cavity 62 may be filled with any suitable material depending on the index of refraction desired, including for example, air or other gases, water, oil, or other transparent liquids, another solid component, or a graded index of refraction material. The material in cavity 62 is also chosen based on the chemical properties of the material. For example, such a material is preferably inert, biocompatible, non-toxic, and suitable for the particular structure and configuration of implant 10.

Figure 8:
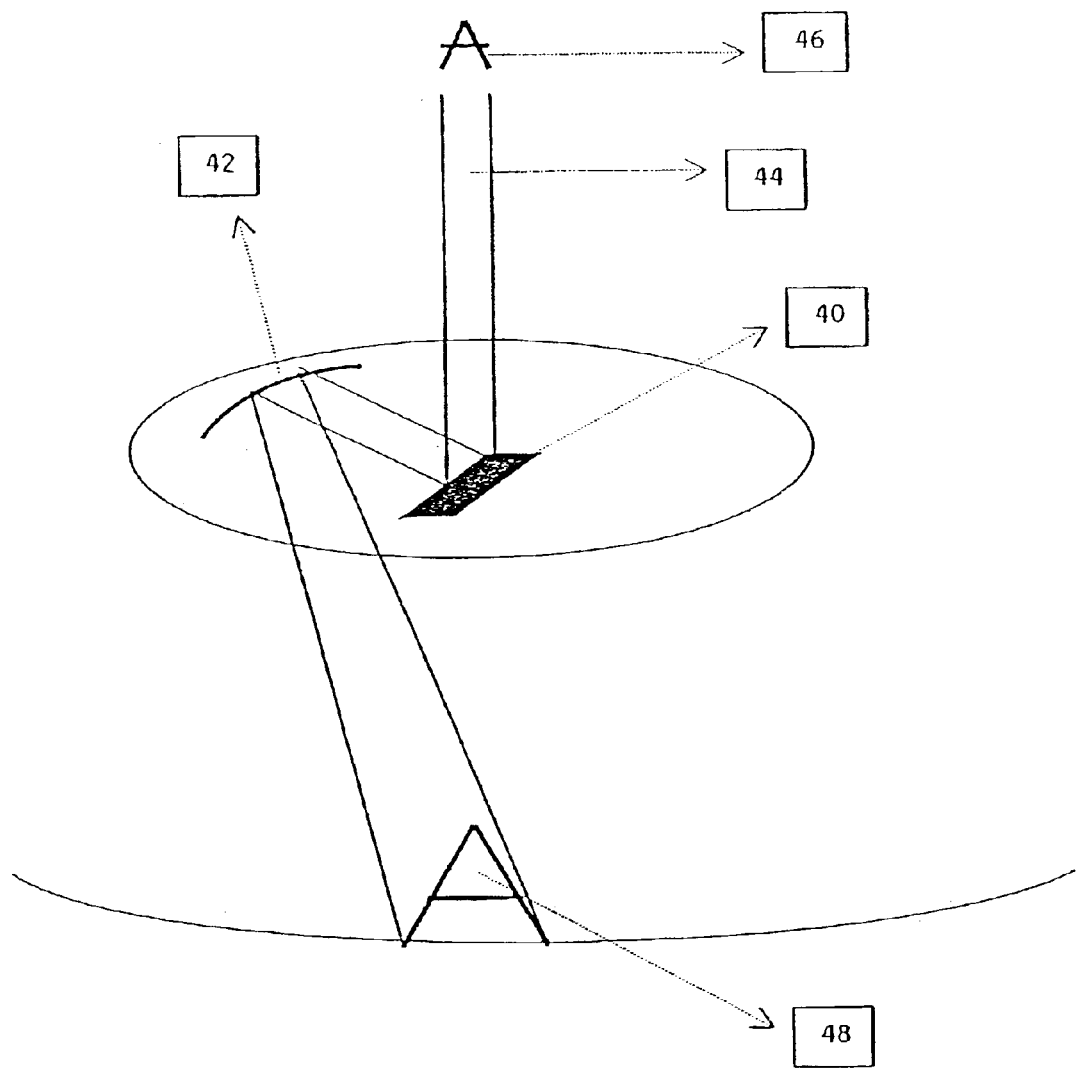
FIG. 8 is a horizontal section of another alternate preferred embodiment of the intraocular insert according to the present invention.

FIG. 8 shows an alternate configuration of implant 10. Such a configuration finds particular use, as non-limiting examples, in the treatment of a regular cataract, and in AMD. In the configuration illustrated in FIG. 8, two mirrors, 40 and 42, are illustrated. Mirror 40 for example has a planar configuration and mirror 42 is not fully circumferential.

Implant 10 according to the present invention can be used in both eyes. As opposed to the intraocular implant with a telescope and the catadioptric intraocular lens of Portnoy there is no interference with the pupil size, peripheral vision and there is no severe anisoconia. In contrast to the intraocular implant with a telescope and the catadioptric intraocular lens of Portnoy, where there is a correlation between the magnification ability, index of refraction of the media and the maximal image size, which confers a limitation, with implant 10 of the present invention, the magnification can be increased, decreased or adapted, and the image size can be increased, decreased or adapted in an unlimited fashion and it does not depend on the index of refraction of the media. Further, treatment with laser or photodynamic therapy can be performed through implant 10, with the laser, for example, passing directly through implant 10 and not through the mirror system, or by reflecting off the at least one mirror. The at least one mirror in some configurations is adapted for transmission of a laser beam for medical purposes. The laser beam may be, for example, PDT, an argon laser, a krypton laser or a YAG laser or any other such laser as is used medically.

In various alternate configurations, implant 10 may find application for uses other than for treating disorders of central vision such as AMD, or those of peripheral vision, such as retinitis pigmentosa. For example, implant 10 may be adapted use to treat a patient suffering from a regular (age-related) cataract or for after cataract surgery. Implant 10 may be used in "healthy" eyes to magnify images, to increase or decrease the amount of light entering, or to change the spectrum of wavelengths and position of light permitted to enter the eye.

Figure 16:
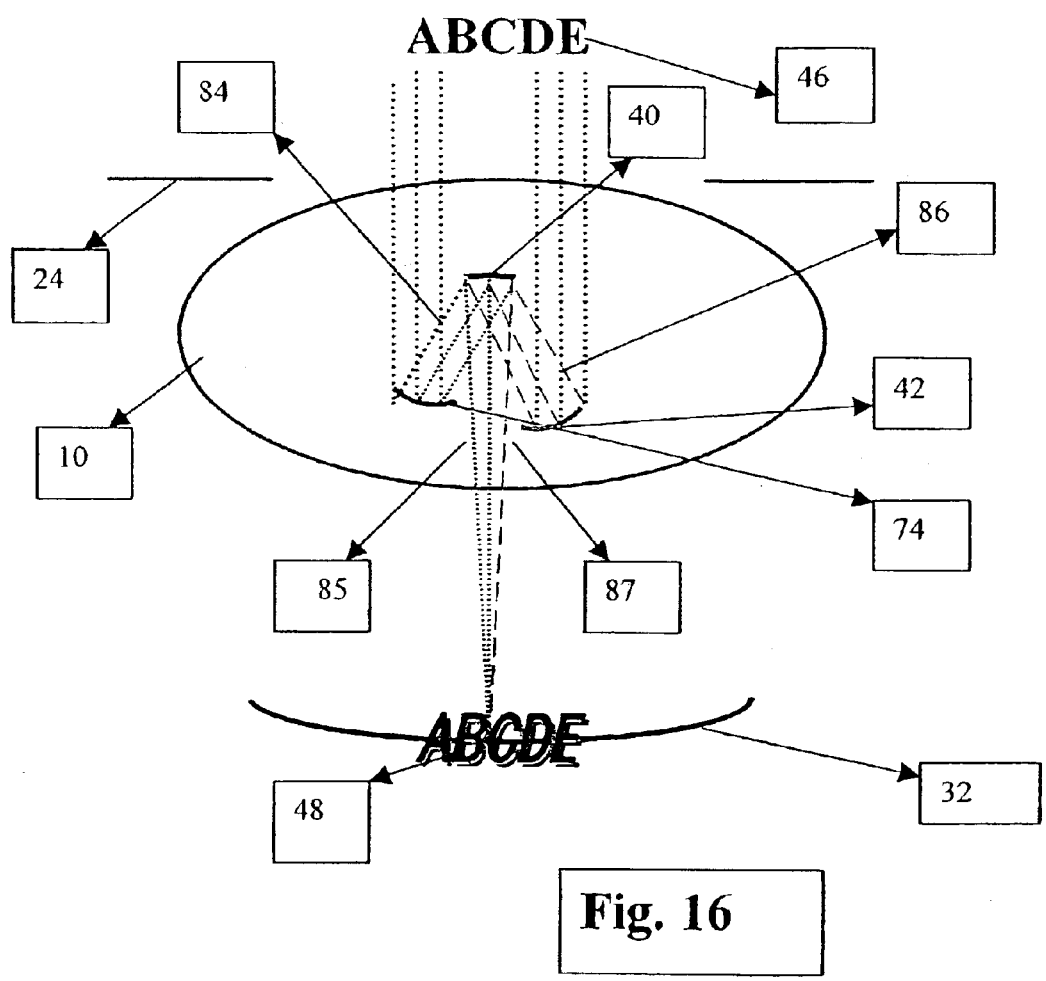
FIG. 16 is a horizontal section of yet another alternate preferred embodiment of the intraocular insert according to the present invention.

FIG. 16 illustrates yet another preferred embodiment of the intraocular implant 10 according to the present invention in which the at least one mirror is employed to divert light within eye 20 to achieve three dimensional visual perception through monocular stereopsis. In the usual circumstance, we achieve three dimensional vision and perception of depth, or stereopsis when the 2 picture images from the two eyes are reflected on the two retinas with a delay in the wave of light between the two eyes. At least one mirror, and preferably at least three mirrors (40, 42 and 74) are placed inside implant 10 in a manner such that two different images will come to be superimposed on the central retina of a single eye 20 with a delay in phase between the two superimposed images. This enables a three dimensional image to be perceived using only one eye, a situation known as monocular stereopsis.

Mirrors 42 and 74 are placed at different specific precise distances from central mirror 40 such that each creates a different image, 48 and 78 respectively on the center (macula) of retina 32 of a single eye 20. Mirrors 42 and 74 create 2 different light paths, 84 and 86 respectively that preferably impact on mirror 40 resulting in reflected rays 85 and 87 respectively which create images 48 and 88 respectively. As images 48 and 88 impact on retina 32 simultaneously and in phase, a three-dimensional image is created and perceived in the brain using only one eye. In other configurations and alternate preferred embodiments monocular stereopsis can also be achieved using additional mirrors to divert at least one image or by placing mirror 40 at a different position or axis relative to mirrors 42 and 74. Alternatively mirrors 42 and 74 may be of different shapes or configurations so as to transmit simultaneously two distinct images 48 and 88 to the same retina 32. As in the previously described preferred embodiments, peripheral vision is preserved.

Figure 17:
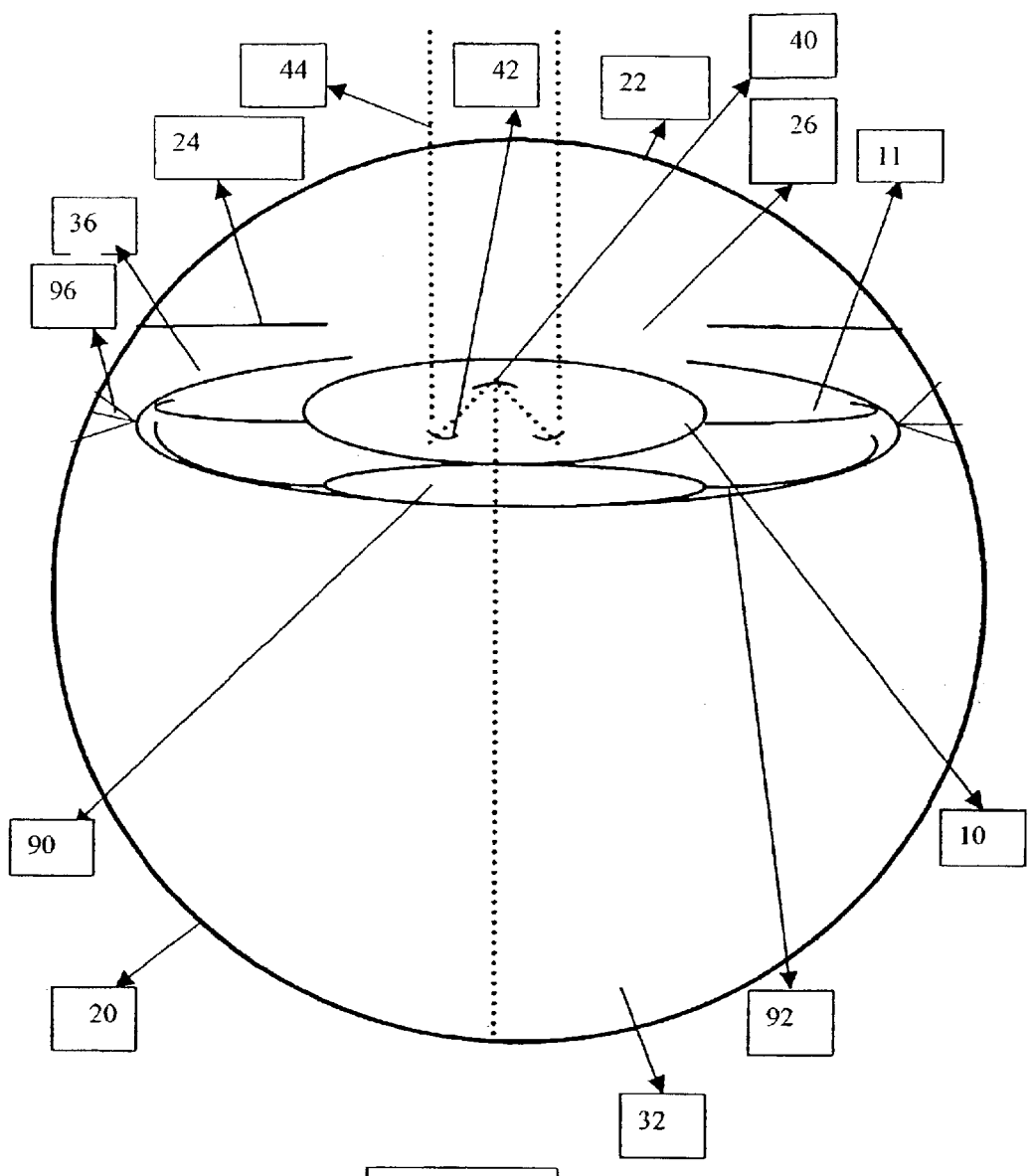
FIG. 17 is a horizontal section of still another alternate preferred embodiment of the intraocular insert according to the present invention.

FIG. 17 illustrates a further preferred embodiment of the present invention. In the preferred embodiment illustrated in FIG. 17, implant 10 is modified in such a way so as to enable it to be implanted in at least one eye which has already undergone surgery, such as for treatment of cataract, with implantation of a "regular" intraocular lens implant. In FIG. 17 capsular bag 36 has been emptied during prior cataract surgery and regular intraocular lens implant 90 has been previously implanted into capsular bag 36 using at least one loop 92. Implant 10 according to the present invention has been subsequently implanted into capsular bag 36 using at least one loop 11 as a "piggy-back implant". While it is known in the art to implant 2 intraocular lens implants into certain eyes, in this case, the second is an implant 10 according to the present invention containing at least one mirror 40. Implant 10 may be implanted to help improve vision in patients who have ARMD or other retinal problems in patients who previously had cataract surgery as non-limiting examples. The exact design and configuration of the arrangement of the at least one mirror may be among the various described herein or any other suitable design for the specific purpose for which implant 10 is employed. The optical performance of implant 10 is calculated in such a way as to take into account the dioptric power of already implanted implant 90. As with previous embodiments, peripheral vision is preserved.

Figure 18:
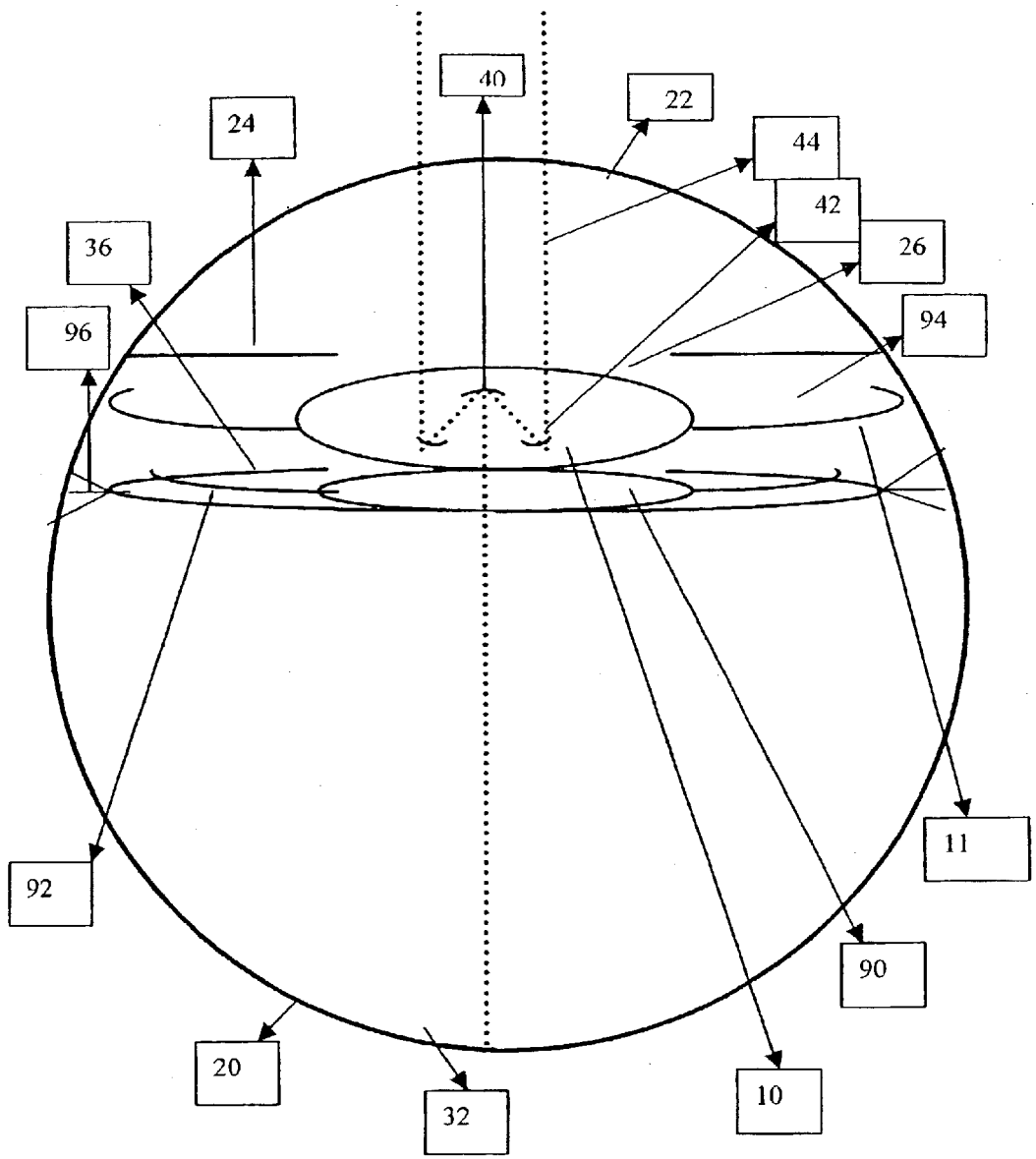
FIG. 18 is a horizontal section of vet another alternate preferred embodiment of the intraocular insert according to the present invention.
Figure 19:
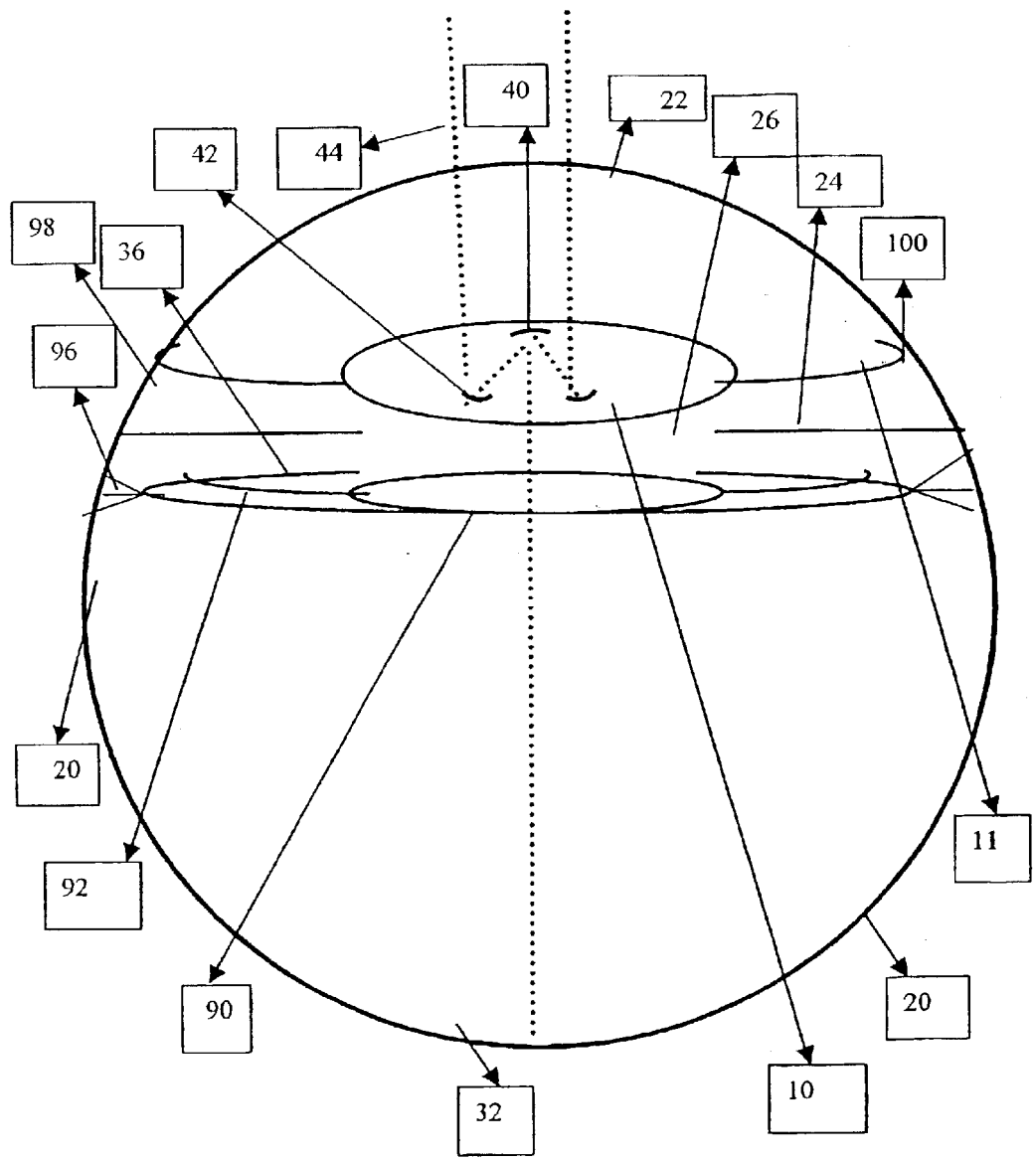
FIG. 19 is a horizontal section of yet another alternate preferred embodiment of the intraocular insert according to the present invention.

FIGS. 18 and 19 illustrate further preferred embodiments of the present invention. In the preferred embodiments illustrated in FIGS. 18 and 19, similar to that in FIG. 17, implant 10 is modified in such a way so as to enable it to be implanted in at least one eye which has already undergone surgery, such as for treatment of cataract, with implantation of a "regular" intraocular lens implant. In the embodiment illustrated in FIG. 18 implant 10 containing at least one mirror 40 according to the present invention is placed in and located in the sulcus 94 so that the at least one loop 11 is located at an angle between iris 24 and ciliary body 96 and not in capsular bag 36. Otherwise implant 10 as illustrated in FIG. 18 is employed and designed in a manner similar to (and optically adapted to) that illustrated in FIG. 17. The preferred embodiment illustrated in FIG. 19 is further identical (and optically adapted to) in all respects to those illustrated in FIGS. 17 and 18, except that implant 10 is placed in the anterior chamber 98 of eye 20. The at least one loop 11 for fixation are located at the anterior chamber angle 100.

Figure 20:
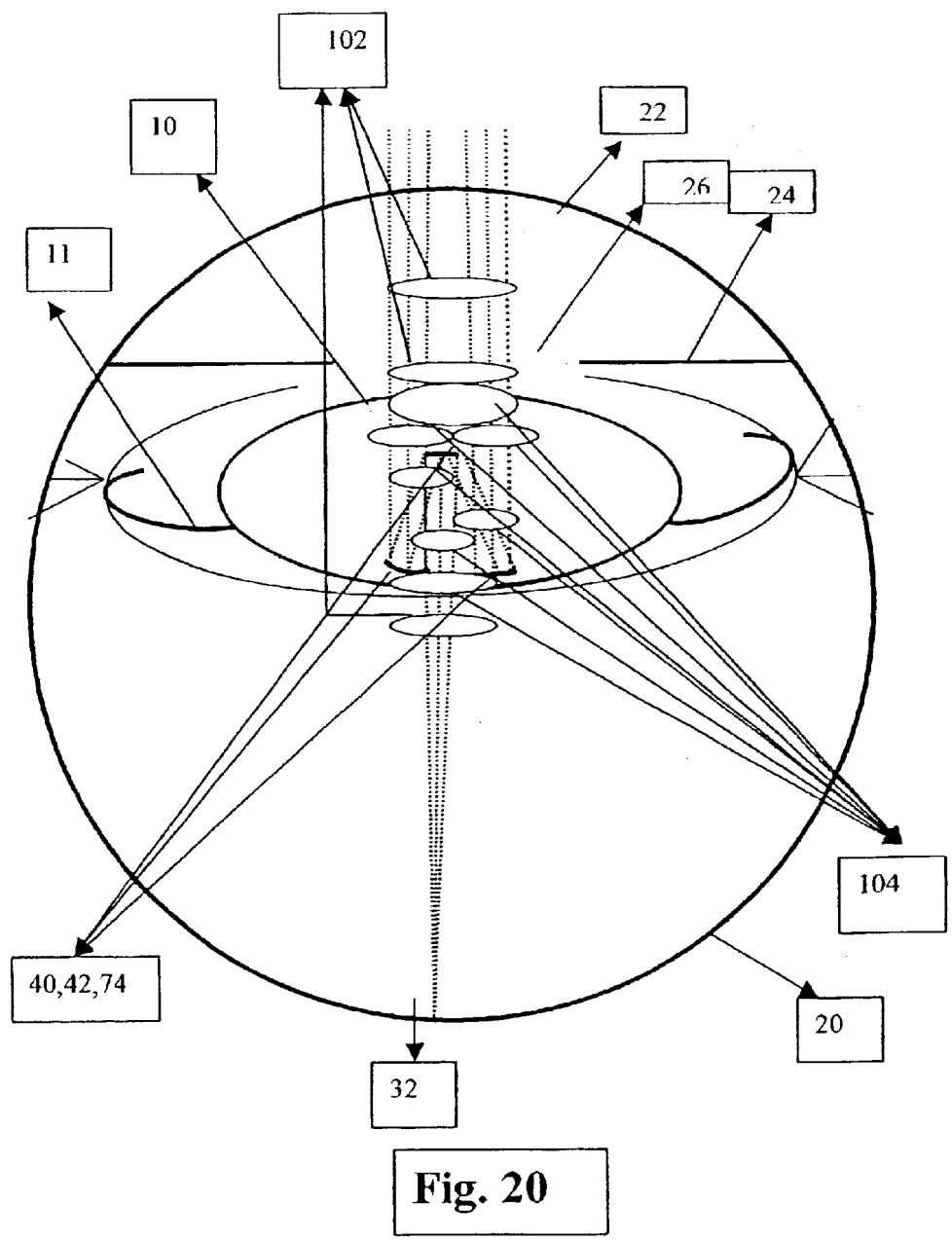
FIG. 20 is a horizontal section of a still further alternate preferred embodiment of the intraocular insert according to the present invention.

FIG. 20 illustrates a further preferred embodiment of the present invention. In the preferred embodiment illustrated in FIG. 20, implant 10 is modified in such a way so as to include at least one lens placed either within or external to implant 10. According to the preferred embodiment illustrated in FIG. 20, the configuration of optical effects is produced not only through use of at least one mirror 40, but also through at least one lens. Multiple lenses are illustrated in FIG. 20 as components 102 and 104. The at least one lens may be introduced at different locations in the optical path of light in different configurations according to the specific purpose of the at least one lens. It can be located before reflecting on the at least one mirror or after reflecting on the at least one mirror, including after all mirrors, or between mirrors, in those configurations with a plurality of mirrors, or any combination thereof. The lenses may be located external to implant 10 as illustrated as lenses 102 or within implant 10 as illustrated in FIG. 20 as 104. Lens 102 may be at any location within eye 20 that is or is not connected to implant 10 or connected only in part. The at least one lens may be employed with implant 10 for purposes including increasing or decreasing magnification, visual field changes, changing of location of the light on the retina, or for improving or inducing optical aberrations, as non-limiting examples. Other optical elements such as a hologram, fresnel, or graded index element, as non-limiting examples, can also be used in place of lenses 102 or 104. The word lens is used to include any optical element that changes the way the light travels.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An intraocular implant for implantation into the interior of an eye, the eye having a pupil, an iris, and a retina, the retina having a macula, the implant comprising:
    a. a body member, said body member having an anterior surface and a posterior surface, said body member having optical properties;
    b. at least one mirror, wherein said at least one mirror is contained within said body member; and c. at least one lens, said at least one lens being operationally connected to said body member, said at least one mirror being disposed externally to said at least one lens.

2. The implant of claim 1, wherein said at least one lens includes a fresnel lens.

3. An intraocular implant for implantation into the interior of an eye, the eye having a pupil, an iris, and a retina, the retina having a macula, the implant comprising:
   a. a body member, said body member having an anterior surface and a posterior surface, said body member having optical properties; and
   b. at least two mirrors, wherein said at least two mirrors are disposed within said body member, said at least two mirrors being arranged such that two images of a single object are formed simultaneously on the retina.

4. An intraocular implant for implantation into the interior of an eye, the eye having a pupil, an iris, and a retina, the retina having a macula, the implant comprising:
   a. a body member, said body member having an anterior surface and a posterior surface, said body member having optical properties;
   b. at least one mirror, wherein said at least one mirror is contained within said body member; and
   c. an adjustment mechanism mechanically connected to said at least one mirror, said adjustment mechanism being configured for adjusting at least one of a position, orientation and curvature of said at least one mirror.

5. An intraocular implant for implantation into the interior of an eye, the eye having a pupil, an iris, and a retina, the retina having a macula, the implant comprising:
   a. a body member, said body member having an anterior surface and a posterior surface, said body member having optical properties;
   b. at least one mirror, wherein said at least one mirror is contained within said body member; and
   c. a prism operationally connected to said body member.

6. An intraocular implant for implantation into the interior of an eye, the eye having a pupil, an iris, and a retina, the retina having a macula, the implant comprising:
   a. a body member configured as a fresnel lens, said body member having an anterior surface and a posterior surface, said body member having optical properties; and
   b. at least one mirror, wherein said at least one mirror is contained within said body member.

* * * * *